US012806358B2

(12) United States Patent
Fox et al.

(10) Patent No.: US 12,806,358 B2
(45) Date of Patent: *Nov. 24, 2026

(54) SYSTEMS AND METHODS FOR IDENTIFYING A USER INTERFACE

(71) Applicant: ResMed Sensor Technologies Limited, Dublin (IE)

(72) Inventors: Niall Andrew Fox, Dublin (IE); Graeme Alexander Lyon, Dublin (IE); Redmond Shouldice, Dublin (IE); Stephen McMahon, Dublin (IE)

(73) Assignee: ResMed Sensor Technologies Limited, Dublin (IE)

( * ) Notice: Subject to any disclaimer, the term of this patent is extended or adjusted under 35 U.S.C. 154(b) by 430 days.

This patent is subject to a terminal disclaimer.

(21) Appl. No.: 18/531,080

(22) Filed: Dec. 6, 2023

(65) Prior Publication Data

US 2024/0173504 A1 May 30, 2024

Related U.S. Application Data

(63) Continuation of application No. 18/000,746, filed as application No. PCT/IB2021/055002 on Jun. 7, 2021, now Pat. No. 11,878,118.

(60) Provisional application No. 63/035,497, filed on Jun. 5, 2020.

(51) Int. Cl.
*A61M 16/06* (2006.01)
*A61M 16/00* (2006.01)

(52) U.S. Cl.
CPC .... *A61M 16/0605* (2014.02); *A61M 16/0069* (2014.02); *A61M 16/024* (2017.08); *A61M 2016/0661* (2013.01); *A61M 2205/3375* (2013.01)

(58) Field of Classification Search
CPC combination set(s) only.
See application file for complete search history.

(56) References Cited

U.S. PATENT DOCUMENTS

| | | | |
|---|---|---|---|
| 5,245,995 | A | 9/1993 | Sullivan et al. |
| 6,502,572 | B1 | 1/2003 | Berthon-Jones et al. |
| 9,358,353 | B2 | 6/2016 | Armitstead et al. |
| 10,492,720 | B2 | 12/2019 | Phillips et al. |
| 10,549,053 | B2 | 2/2020 | Armitstead et al. |

(Continued)

FOREIGN PATENT DOCUMENTS

| | | | |
|---|---|---|---|
| AU | 2014271343 | A1 | 1/2015 |
| JP | 2013514821 | A | 5/2013 |

(Continued)

OTHER PUBLICATIONS

Ayappa et al., "Non-Invasive Detection of Respiratory Effort-Related Arousals (RERAs) by a Nasal Cannula/Pressure Transducer System" done at NYU School of Medicine and published in Sleep, vol. 23, No. 6, pp. 763-771.

(Continued)

*Primary Examiner* — Margaret M Luarca
(74) *Attorney, Agent, or Firm* — Nixon Peabody LLP

(57) ABSTRACT

The present disclosure relates to a method for identifying a user interface. Flow data associated with air flowing in a respiratory therapy system is received. Acoustic data associated with the respiratory therapy system is received. The received flow data and the received acoustic data are analyzed. Based at least in part on the analysis, a mask type for the user interface is determined.

20 Claims, 14 Drawing Sheets

(56) References Cited

U.S. PATENT DOCUMENTS

| | | | |
|---|---|---|---|
| 10,660,563 | B2 | 5/2020 | Mcdarby et al. |
| 2011/0313689 | A1 | 12/2011 | Holley et al. |
| 2012/0247470 | A1 | 10/2012 | Ho et al. |
| 2013/0179061 | A1 | 7/2013 | Gadh et al. |
| 2017/0311879 | A1 | 11/2017 | Armitstead et al. |
| 2020/0001030 | A1 | 1/2020 | Grashow et al. |
| 2020/0143915 | A1 | 5/2020 | Semen et al. |
| 2020/0197640 | A1 | 6/2020 | Armitstead et al. |
| 2020/0337634 | A1 | 10/2020 | Mcdarby et al. |
| 2020/0383580 | A1 | 12/2020 | Shouldice et al. |
| 2021/0150873 | A1 | 5/2021 | Shouldice et al. |
| 2023/0417544 | A1 | 12/2023 | Lyon et al. |

FOREIGN PATENT DOCUMENTS

| | | | |
|---|---|---|---|
| WO | 2008138040 | A1 | 11/2008 |
| WO | 2012012835 | A2 | 2/2012 |
| WO | 2014047310 | A1 | 3/2014 |
| WO | 2016061629 | A1 | 4/2016 |
| WO | 2017132726 | A1 | 8/2017 |
| WO | 2018050913 | A1 | 3/2018 |
| WO | 2019122412 | A1 | 6/2019 |
| WO | 2019122413 | A1 | 6/2019 |
| WO | 2019122414 | A1 | 6/2019 |
| WO | 2020092701 | A2 | 5/2020 |
| WO | 2020104465 | A2 | 5/2020 |
| WO | 2021176426 | A1 | 9/2021 |
| WO | 2021250553 | | 12/2021 |

OTHER PUBLICATIONS

Childers et al., “The Cepstrum: A Guide to Processing”, Proceedings of the IEEE, vol. 65, No. 10, Oct. 1977, pp. 1428-1443.

Randall R.B., Frequency Analysis, Copenhagen: Bruel & Kjaer, p. 344 (1977, revised ed. 1987).

International Preliminary Report on Patentability Chapter IIin International Patent Application No. PCT/IB2021/055002 mailed Jan. 4, 2022 (32 pp.).

Written Opinion in International Patent Application No. PCT/IB2021/055002 mailed Jul. 30, 2021 (9 pp.).

International Search Report in International Patent Application No. PCT/IB2021/055002 mailed Jul. 30, 2021 (3 pp.).

SYSTEMS AND METHODS FOR IDENTIFYING A USER INTERFACE

CROSS-REFERENCE TO RELATED APPLICATIONS

This application is a continuation of U.S. patent application Ser. No. 18/000,746, filed Dec. 5, 2022, now allowed, which is a U.S. National Stage of International Application No. PCT/IB2021/055002, filed on Jun. 7, 2021, which claims the benefit of, and priority to, U.S. Provisional Patent Application No. 63/035,497 filed on Jun. 5, 2020, each of which is hereby incorporated by reference herein in its entirety.

TECHNICAL FIELD

The present disclosure relates generally to systems and methods for identifying a user interface, and more particularly, to systems and methods for determining a mask type for the user interface.

BACKGROUND

Many individuals suffer from sleep-related and/or respiratory disorders such as, for example, Periodic Limb Movement Disorder (PLMD), Restless Leg Syndrome (RLS), Sleep-Disordered Breathing (SDB), such as Obstructive Sleep Apnea (OSA), Central Sleep Apnea (CSA), and other types of apneas such as mixed apneas and hypopneas, Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hypertension, diabetes, stroke, insomnia, and chest wall disorders. These disorders are often treated using a respiratory therapy system. A person with respiratory disorder can have trouble sleeping, but systems designed to mitigate physical symptoms of the respiratory disorder do not address issues outside of the symptoms of the disorder itself that can keep the person from sleeping well.

For example, each respiratory therapy system generally has a respiratory therapy device connected to a user interface (sometimes referred to as a mask) via a conduit. The user wears the user interface and is supplied a flow of pressurized air from the respiratory therapy device via the conduit.

A variety of different user interfaces can be used. The user interface generally is a specific category and type of user interface for the user, such as direct connections (e.g., conduit connected to cushion and/or frame of user interface) or indirect connections (e.g., conduit connected into a chamber formed by cushion and/or frame) for the category of user interface, and full face mask, a partial face mask (e.g., a mask which covers the mouth but does not cover the nose or only covers a portion of the nose), nasal mask, or nasal pillows for the type of user interface. In addition to the specific category and type, the user interface generally is a specific model made by a specific manufacturer. For example, each type of user interface can have different models made by the same manufacturer, with each model varying in shape, size, aesthetic style, manufacturing date, etc. In some implementations, different forms of air delivery conduit may also be used. It is advantageous to know the user interface and conduit connected to a respiratory therapy device for providing improved control of therapy delivered to the user. For instance, it may be advantageous in the measurement or estimation of treatment parameters, such as pressure in the mask and vent flow. Accordingly, knowledge, or confirmation, of what user interface is being used can enhance therapy. Although respiratory devices may include a menu system that allows a user to enter the type of user interface being used, e.g., by type, model, manufacturer, etc., the user may enter incorrect or incomplete information. Thus, a need exists for systems and methods for identifying the specific type of mask associated with the respiratory therapy system. The present disclosure is directed to solving these problems and addressing other needs.

SUMMARY

According to some implementations of the present disclosure, a method for identifying a user interface is described. Flow data associated with air flowing in a respiratory therapy system is received. Acoustic data associated with the respiratory therapy system is received. The received flow data and the received acoustic data are analyzed. Based at least in part on the analysis, a mask type for the user interface is determined.

According to some implementations of the present disclosure, a system includes a control system having one or more processors, and a memory having stored thereon machine readable instructions. The control system is coupled to the memory. The method disclosed above is implemented when the machine executable instructions in the memory are executed by at least one of the one or more processors of the control system.

According to some implementations of the present disclosure, a system for identifying a user interface includes a control system having one or more processors configured to implement the method disclosed above.

According to some implementations of the present disclosure, a computer program product includes instructions which, when executed by a computer, cause the computer to carry out the method disclosed above. In some implementations, the computer program product is a non-transitory computer readable medium.

The above summary is not intended to represent each implementation or every aspect of the present disclosure. Additional features and benefits of the present disclosure are apparent from the detailed description and figures set forth below.

BRIEF DESCRIPTION OF THE DRAWINGS

The foregoing and other advantages of the present disclosure will become apparent upon reading the following detailed description and upon reference to the drawings.

Figure 1:
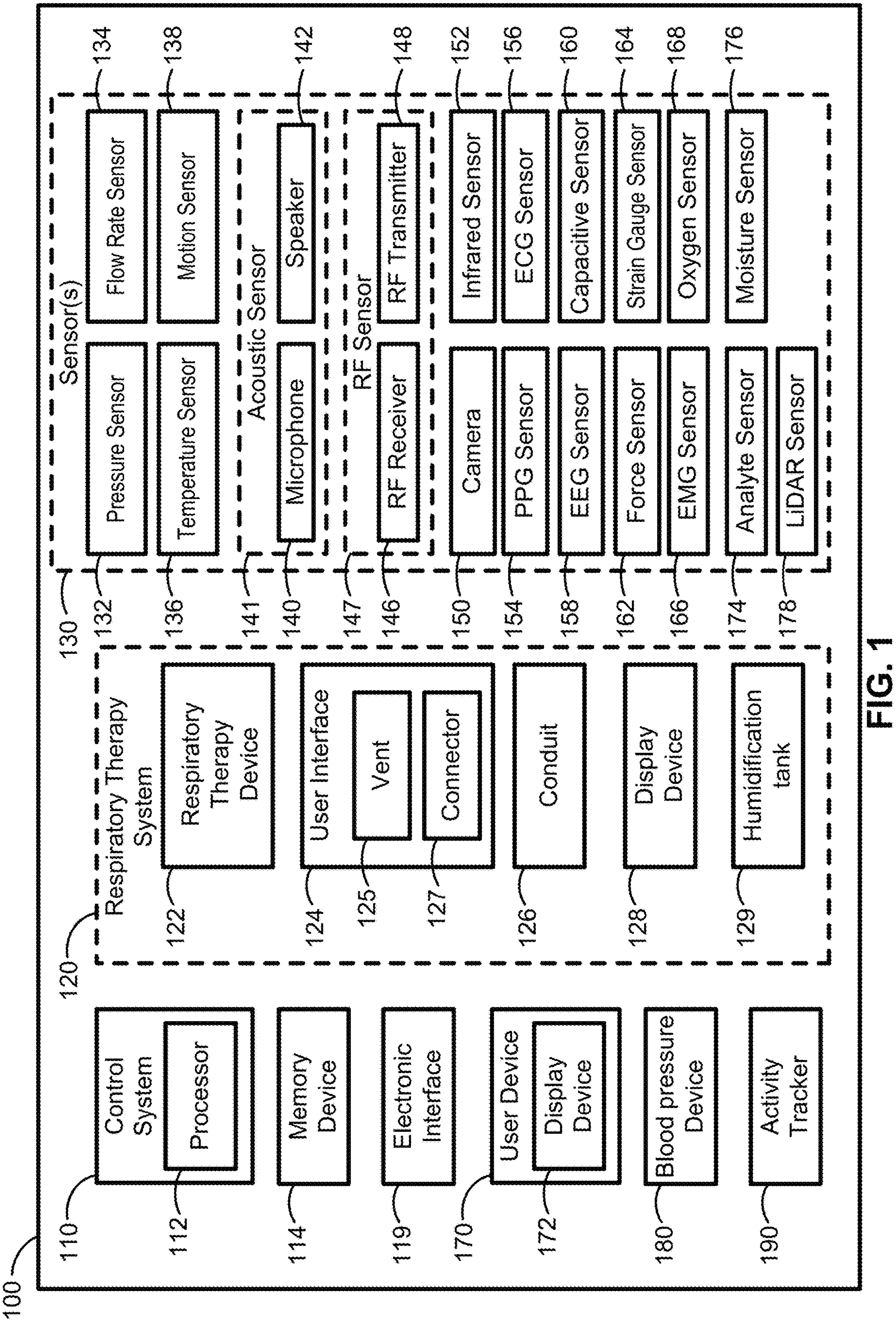
FIG. 1 is a functional block diagram of a system, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

The present disclosure is described with reference to the attached figures, where like reference numerals are used throughout the figures to designate similar or equivalent elements. The figures are not drawn to scale, and are provided merely to illustrate the instant disclosure. Several aspects of the disclosure are described below with reference to example applications for illustration.

Many individuals suffer from sleep-related and/or respiratory-related disorders such as, for example, Periodic Limb Movement Disorder (PLMD), Restless Leg Syndrome (RLS), Sleep-Disordered Breathing (SDB) such as Obstructive Sleep Apnea (OSA), Central Sleep Apnea (CSA), and other types of apneas such as mixed apneas and hypopneas, Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hyper tension, diabetes, stroke, insomnia, and chest wall disorders.

Obstructive Sleep Apnea (OSA) is a form of Sleep Disordered Breathing (SDB), and is characterized by events including occlusion or obstruction of the upper air passage during sleep resulting from a combination of an abnormally small upper airway and the normal loss of muscle tone in the region of the tongue, soft palate and posterior oropharyngeal wall.

Central Sleep Apnea (CSA) is another form of SDB that results when the brain temporarily stops sending signals to the muscles that control breathing. More generally, an apnea generally refers to the cessation of breathing caused by blockage of the air or the stopping of the breathing function. Typically, the individual will stop breathing for between about 15 seconds and about 30 seconds during an obstructive sleep apnea event. Mixed sleep apnea is another form of SDB that is a combination of OSA and CSA.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

A Respiratory Effort Related Arousal (RERA) event is typically characterized by an increased respiratory effort for 10 seconds or longer leading to arousal from sleep and which does not fulfill the criteria for an apnea or hypopnea event. In 1999, the AASM Task Force defined RERAs as "a sequence of breaths characterized by increasing respiratory effort leading to an arousal from sleep, but which does not meet criteria for an apnea or hypopnea. These events must fulfil both of the following criteria: 1. pattern of progressively more negative esophageal pressure, terminated by a sudden change in pressure to a less negative level and an arousal; 2. the event lasts 10 seconds or longer. In 2000, the study "Non-Invasive Detection of Respiratory Effort-Related Arousals (RERAs) by a Nasal Cannula/Pressure Transducer System" done at NYU School of Medicine and published in Sleep, vol. 23, No. 6, pp. 763-771, demonstrated that a Nasal Cannula/Pressure Transducer System was adequate and reliable in the detection of RERAs. A RERA detector may be based on a real flow signal derived from a respiratory therapy (e,g, PAP) device. For example, a flow limitation measure may be determined based on a flow signal. A measure of arousal may then be derived as a function of the flow limitation measure and a measure of sudden increase in ventilation. One such method is described in WO 2008/138040, US 9,358,353, U.S. Pat. No. 10,549,053, and US 2020/0197640, each of which is hereby incorporated by reference herein in its entirety.

Cheyne-Stokes Respiration (CSR) is another form of SDB. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

Generally, a user who is prescribed usage of a respiratory therapy system will tend to experience higher quality sleep and less fatigue during the day after using the respiratory therapy system during the sleep compared to not using the respiratory therapy system (especially when the user suffers from sleep apnea or other sleep related disorders). However, many users do not conform to their prescribed usage because the user interface is uncomfortable or cumbersome (e.g., due to improperly fitted user interface and/or wrong settings associated with the user interface), or due to other side effects (e.g., dry mouth, dry lips, dry throat, discomfort, etc.). Users are more likely to fail to use the respiratory therapy system as prescribed (or discontinue usage altogether) if they fail to perceive that they are experiencing any benefits (e.g., less fatigue during the day).

Referring to FIG. 1, a system 100, according to some implementations of the present disclosure, is illustrated. The system 100 can be used to identify a user interface used by a user, among other uses. The system 100 includes a control system 110, a memory device 114, an electronic interface 119, one or more sensors 130, and optionally one or more user devices 170. In some implementation, the system 100 further includes a respiratory therapy system 120 that includes a respiratory therapy device 122. The system 100 can be used to detect and/or identify a user interface 124, as disclosed in further detail herein.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 (or any other control system) or a portion of the control system 110 such as the processor 112 (or any other processor(s) or portion(s) of any other control system), can be used to carry out one or more steps of any of the methods described and/or claimed herein. The control system 110 can be coupled to and/or positioned within, for example, a housing of the user device 170, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory therapy device 122 of the respiratory therapy system 120, within a housing of the user device 170, within a housing of one or more of the sensors 130, or any combination thereof. Like the control system 110, the memory device 114 can be centralized (within one such housing) or decentralized (within two or more of such housings, which are physically distinct).

In some implementations, the memory device 114 stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family medical history (such as a family history of insomnia or sleep apnea), an employment status of the user, an educational status of the user, a socioeconomic status of the user, or any combination thereof. The medical information can include, for example, information indicative of one or more medical conditions associated with the user, medication usage by the user, or both. The medical information data can further include a fall risk assessment associated with the user (e.g., a fall risk score using the Morse fall scale), a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data and/or acoustic data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a WiFi communication protocol, a Bluetooth communication protocol, an IR communication protocol, over a cellular network, over any other optical communication protocol, etc.). The electronic interface 119 can include an antenna, a receiver (e.g., an RF receiver), a transmitter (e.g., an RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the user device 170. In other implementations, the electronic interface 119 is coupled to or integrated (e.g., in a housing) with the control system 110 and/or the memory device 114.

As noted above, in some implementations, the system 100 optionally includes a respiratory therapy system 120 (also referred to as a respiratory pressure therapy system). The respiratory therapy system 120 can include a respiratory therapy device 122 (also referred to as a respiratory pressure device), a user interface 124 (also referred to as a mask or a patient interface), a conduit 126 (also referred to as a tube or an air circuit), a display device 128, a humidification tank 129, or any combination thereof. In some implementations, the control system 110, the memory device 114, the display device 128, one or more of the sensors 130, and the humidification tank 129 are part of the respiratory therapy device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 120 is generally used to treat individuals suffering from one or more sleep-related respiratory disorders (e.g., obstructive sleep apnea, central sleep apnea, or mixed sleep apnea), other respiratory disorders such as COPD, or other disorders leading to respiratory insufficiency, that may manifest either during sleep or wakefulness.

The respiratory therapy device 122 is generally used to generate pressurized air that is delivered to a user (e.g., using one or more motors that drive one or more compressors). In some implementations, the respiratory therapy device 122 generates continuous constant air pressure that is delivered to the user. In other implementations, the respiratory therapy device 122 generates two or more predetermined pressures (e.g., a first predetermined air pressure and a second predetermined air pressure). In still other implementations, the respiratory therapy device 122 is configured to generate a variety of different air pressures within a predetermined range. For example, the respiratory therapy device 122 can deliver at least about 6 cm $H_2O$, at least about 10 cm $H_2O$, at least about 20 cm $H_2O$, between about 6 cm $H_2O$, and about 10 cm $H_2O$, between about 7 cm $H_2O$ and about 12 cm $H_2O$ etc. The respiratory therapy device 122 can also deliver pressurized air at a predetermined flow rate between, for example, about −20 L/min and about 150 L/min, while maintaining a positive pressure (relative to the ambient pressure). In some implementations, the control system 110, the memory device 114, the electronic interface 119, or any combination thereof can be coupled to and/or positioned within a housing of the respiratory therapy device 122.

The user interface 124 engages a portion of the user's face and delivers pressurized air from the respiratory therapy device 122 to the user's airway to aid in preventing the airway from narrowing and/or collapsing during sleep. This may also increase the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 $cmH_2O$.

Figure 2:
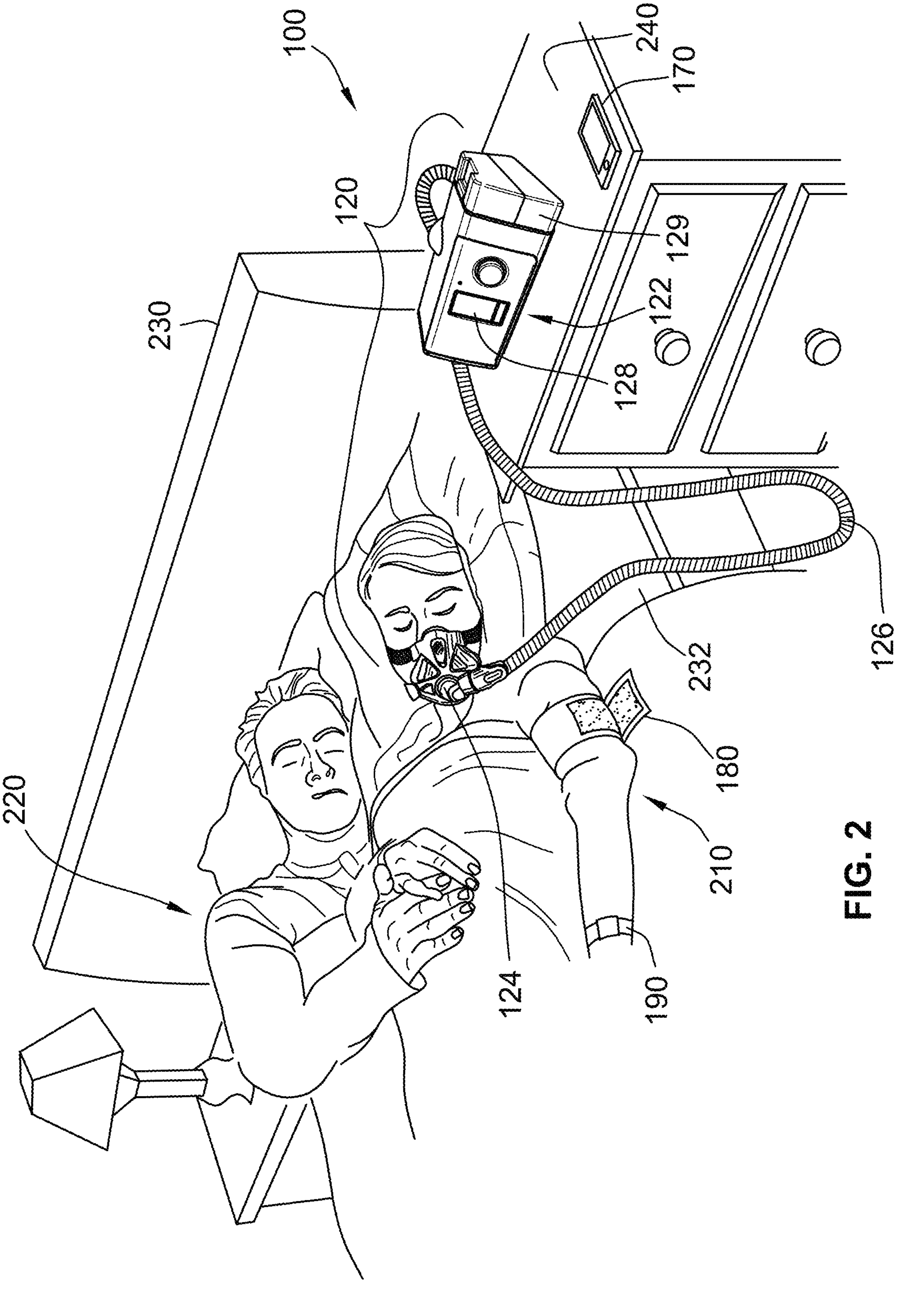
FIG. 2 is a perspective view of at least a portion of the system of FIG. 1, a user wearing a full face mask, and a bed partner, according to some implementations of the present disclosure.

In some implementations, the user interface 124 is or includes a facial mask that covers the nose and mouth of the user (as shown, for example, in FIG. 2). Alternatively, the user interface 124 is or includes a nasal mask that provides air to the nose of the user or a nasal pillow mask that delivers air directly to the nostrils of the user. The user interface 124 can include a strap assembly that has a plurality of straps (e.g., including hook and loop fasteners) for positioning and/or stabilizing the user interface 124 on a portion of the user interface 124 on a desired location of the user (e.g., the face), and a conformal cushion (e.g., silicone, plastic, foam, etc.) that aids in providing an air-tight seal between the user interface 124 and the user. In some implementations, the user interface 124 may include a connector 127 and one or more vents 125. The one or more vents 125 can be used to permit the escape of carbon dioxide and other gases exhaled by the user. In other implementations, the user interface 124 includes a mouthpiece (e.g., a night guard mouthpiece molded to conform to the user's teeth, a mandibular repositioning device, etc.). In some implementations, the connector 127 is distinct from, but couplable to, the user interface 124 (and/or conduit 126). The connector 127 is configured to connect and fluidly couple the user interface 124 to the conduit 126.

The conduit 126 allows the flow of air between two components of a respiratory therapy system 120, such as the respiratory therapy device 122 and the user interface 124. In some implementations, there can be separate limbs of the conduit for inhalation and exhalation. In other implementations, a single limb conduit is used for both inhalation and exhalation. Generally, the respiratory therapy system 120 forms an air pathway that extends between a motor of the respiratory therapy device 122 and the user and/or the user's airway. Thus, the air pathway generally includes at least a motor of the respiratory therapy device 122, the user interface 124, and the conduit 126.

One or more of the respiratory therapy device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be used, for example, to measure the air pressure and/or flow rate of pressurized air supplied by the respiratory therapy device 122.

The display device 128 is generally used to display image(s) including still images, video images, or both and/or information regarding the respiratory therapy device 122.

For example, the display device 128 can provide information regarding the status of the respiratory therapy device 122 (e.g., whether the respiratory therapy device 122 is on/off, the pressure of the air being delivered by the respiratory therapy device 122, the temperature of the air being delivered by the respiratory therapy device 122, etc.) and/or other information (e.g., a sleep score or a therapy score (such as a myAir™ score, such as described in WO 2016/061629 and US 2017/0311879, each of which is hereby incorporated by reference herein in its entirety), the current date/time, personal information for the user, a questionnaire for the user, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 122.

The humidification tank 129 is coupled to or integrated in the respiratory therapy device 122 and includes a reservoir of water that can be used to humidify the pressurized air delivered from the respiratory therapy device 122. The respiratory therapy device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user. The humidification tank 129 can be fluidly coupled to a water vapor inlet of the air pathway and deliver water vapor into the air pathway via the water vapor inlet, or can be formed in-line with the air pathway as part of the air pathway itself. In other implementations, the respiratory therapy device 122 or the conduit 126 can include a waterless humidifier. The waterless humidifier can incorporate sensors that interface with other sensor positioned elsewhere in system 100.

The respiratory therapy system 120 can be used, for example, as a ventilator or a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based at least in part on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 2, a portion of the system 100 (FIG. 1), according to some implementations, is illustrated. A user 210 of the respiratory therapy system 120 and a bed partner 220 are located in a bed 230 and are laying on a mattress 232. The user interface 124 (e.g., a full facial mask) can be worn by the user 210 during a sleep session. The user interface 124 is fluidly coupled and/or connected to the respiratory therapy device 122 via the conduit 126. In turn, the respiratory therapy device 122 delivers pressurized air to the user 210 via the conduit 126 and the user interface 124 to increase the air pressure in the throat of the user 210 to aid in preventing the airway from closing and/or narrowing during sleep. The respiratory therapy device 122 can include the display device 128, which can allow the user to interact with the respiratory therapy device 122. The respiratory therapy device 122 can also include the humidification tank 129, which stores the water used to humidify the pressurized air. The respiratory therapy device 122 can be positioned on a nightstand 240 that is directly adjacent to the bed 230 as shown in FIG. 2, or more generally, on any surface or structure that is generally adjacent to the bed 230 and/or the user 210. The user can also wear the blood pressure device 180 and the activity tracker 190 while lying on the mattress 232 in the bed 230.

Referring back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, an RF transmitter 148, a camera 150, an infrared (IR) sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a light detection and ranging (LiDAR) sensor 178, or any combination thereof. Generally, each of the one or sensors 130 are configured to output sensor data that is received and stored in the memory device 114 or one or more other memory devices. The sensors 130 can also include, an electrooculography (EOG) sensor, a peripheral oxygen saturation ($SpO_2$) sensor, a galvanic skin response (GSR) sensor, a carbon dioxide ($CO_2$) sensor, or any combination thereof.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the IR sensor 152, the PPG sensor 154, the ECG sensor 156, the EEG sensor 158, the capacitive sensor 160, the force sensor 162, the strain gauge sensor 164, the EMG sensor 166, the oxygen sensor 168, the analyte sensor 174, the moisture sensor 176, and the LiDAR sensor 178, more generally, the one or more sensors 130 can include any combination and any number of each of the sensors described and/or shown herein.

The one or more sensors 130 can be used to generate, for example physiological data, acoustic data, or both, that is associated with a user of the respiratory therapy system 120 (such as the user 210 of FIG. 2), the respiratory therapy system 120, both the user and the respiratory therapy system 120, or other entities, objects, activities, etc. Physiological data generated by one or more of the sensors 130 can be used by the control system 110 to determine a sleep-wake signal associated with the user during the sleep session and one or more sleep-related parameters. The sleep-wake signal can be indicative of one or more sleep stages (sometimes referred to as sleep states), including sleep, wakefulness, relaxed wakefulness, micro-awakenings, or distinct sleep stages such as a rapid eye movement (REM) stage (which can include both a typical REM stage and an atypical REM stage), a first non-REM stage (often referred to as "N1"), a second non-REM stage (often referred to as "N2"), a third non-REM stage (often referred to as "N3"), or any combination thereof. Methods for determining sleep stages from physiological data generated by one or more of the sensors, such as sensors 130, are described in, for example, WO 2014/047310, U.S. Pat. Nos. 10,492,720, 10,660,563, US 2020/0337634, WO 2017/132726, WO 2019/122413, US 2021/0150873, WO 2019/122414, US 2020/0383580, each of which is hereby incorporated by reference herein in its entirety.

The sleep-wake signal can also be timestamped to indicate a time that the user enters the bed, a time that the user exits the bed, a time that the user attempts to fall asleep, etc. The sleep-wake signal can be measured one or more of the sensors 130 during the sleep session at a predetermined sampling rate, such as, for example, one sample per second, one sample per 30 seconds, one sample per minute, etc. Examples of the one or more sleep-related parameters that can be determined for the user during the sleep session based at least in part on the sleep-wake signal include a total time in bed, a total sleep time, a total wake time, a sleep onset latency, a wake-after-sleep-onset parameter, a sleep efficiency, a fragmentation index, an amount of time to fall asleep, a consistency of breathing rate, a fall asleep time, a wake time, a rate of sleep disturbances, a number of movements, or any combination thereof.

Physiological data and/or acoustic data generated by the one or more sensors 130 can also be used to determine a respiration signal associated with the user during a sleep session. The respiration signal is generally indicative of respiration or breathing of the user during the sleep session. The respiration signal can be indicative of, for example, a respiration rate, a respiration rate variability, an inspiration amplitude, an expiration amplitude, an inspiration-expiration amplitude ratio, an inspiration-expiration duration ratio, a number of events per hour, a pattern of events, pressure settings of the respiratory therapy device 122, or any combination thereof. The event(s) can include snoring, apneas, central apneas, obstructive apneas, mixed apneas, hypopneas, RERAs, a flow limitation (e.g., an event that results in the absence of the increase in flow despite an elevation in negative intrathoracic pressure indicating increased effort), a mask leak (e.g., from the user interface 124), a restless leg, a sleeping disorder, choking, an increased heart rate, a heart rate variation, labored breathing, an asthma attack, an epileptic episode, a seizure, a fever, a cough, a sneeze, a snore, a gasp, the presence of an illness such as the common cold or the flu, an elevated stress level, etc. Events can be detected by any means known in the art such as described in, for example, U.S. Pat. Nos. 5,245,995, 6,502,572, WO 2018/050913, WO 2020/104465, each of which is incorporated by reference herein in its entirety.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory therapy system 120 and/or ambient pressure. In such implementations, the pressure sensor 132 can be coupled to or integrated in the respiratory therapy device 122. The pressure sensor 132 can be, for example, a capacitive sensor, an electromagnetic sensor, an inductive sensor, a resistive sensor, a piezoelectric sensor, a strain-gauge sensor, an optical sensor, a potentiometric sensor, or any combination thereof. In one example, the pressure sensor 132 can be used to determine a blood pressure of the user.

The flow rate sensor 134 outputs flow rate data that can be stored in the memory device 114 and/or analyzed by the processor 112 of the control system 110. In some implementations, the flow rate sensor 134 is used to determine an air flow rate from the respiratory therapy device 122, an air flow rate through the conduit 126, an air flow rate through the user interface 124, or any combination thereof. In such implementations, the flow rate sensor 134 can be coupled to or integrated in the respiratory therapy device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The temperature sensor 136 outputs temperature data that can be stored in the memory device 114 and/or analyzed by the processor 112 of the control system 110. In some implementations, the temperature sensor 136 generates temperatures data indicative of a core body temperature of the user, a skin temperature of the user 210, a temperature of the air flowing from the respiratory therapy device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The motion sensor 138 outputs motion data that can be stored in the memory device 114 and/or analyzed by the processor 112 of the control system 110. The motion sensor 138 can be used to detect movement of the user during the sleep session, and/or detect movement of any of the components of the respiratory therapy system 120, such as the respiratory therapy device 122, the user interface 124, or the conduit 126. The motion sensor 138 can include one or more inertial sensors, such as accelerometers, gyroscopes, and magnetometers. The motion sensor 138 can be used to detect motion or acceleration associated with arterial pulses, such as pulses in or around the face of the user and proximal to the user interface 124, and configured to detect features of the pulse shape, speed, amplitude, or volume. In some implementations, the motion sensor 138 alternatively or additionally generates one or more signals representing bodily movement of the user, from which may be obtained a signal representing a sleep state of the user; for example, via a respiratory movement of the user.

The microphone 140 outputs acoustic data that can be stored in the memory device 114 and/or analyzed by the processor 112 of the control system 110. The acoustic data generated by the microphone 140 is reproducible as one or more sound(s) during a sleep session (e.g., sounds from the user) to determine (e.g., using the control system 110) one or more sleep-related parameters, as described in further detail herein. The acoustic data from the microphone 140 can also be used to identify (e.g., using the control system 110) an event experienced by the user during the sleep session, as described in further detail herein. In other implementations, the acoustic data from the microphone 140 is representative of noise associated with the respiratory therapy system 120. In some implementations, the system 100 includes a plurality of microphones (e.g., two or more microphones and/or an array of microphones with beamforming) such that sound data generated by each of the plurality of microphones can be used to discriminate the sound data generated by another of the plurality of microphones. The microphone 140 can be coupled to or integrated in the respiratory therapy system 120 (or the system 100) generally in any configuration. For example, the microphone 140 can be disposed inside the respiratory therapy device 122, the user interface 124, the conduit 126, or other components. The microphone 140 can also be positioned adjacent to or coupled to the outside of the respiratory therapy device 122, the outside of the user interface 124, the outside of the conduit 126, or outside of any other components. The microphone 140 could also be a component of the user device 170 (e.g., the microphone 140 is a microphone of a smart phone). The microphone 140 can be integrated into the user interface 124, the conduit 126, the respiratory therapy device 122, or any combination thereof. In general, the microphone 140 can be located at any point within or adjacent to the air pathway of the respiratory therapy system 120, which includes at least the motor of the respiratory therapy device 122, the user interface 124, and the conduit 126. Thus, the air pathway can also be referred to as the acoustic pathway.

The speaker 142 outputs sound waves that are audible to the user. In one or more implementations, the sound waves can be audible to a user of the system 100 or inaudible to the user of the system (e.g., ultrasonic sound waves). The speaker 142 can be used, for example, as an alarm clock or to play an alert or message to the user (e.g., in response to an event). In some implementations, the speaker 142 can be used to communicate the acoustic data generated by the microphone 140 to the user. The speaker 142 can be coupled to or integrated in the respiratory therapy device 122, the user interface 124, the conduit 126, or the user device 170.

The microphone 140 and the speaker 142 can be used as separate devices. In some implementations, the microphone 140 and the speaker 142 can be combined into an acoustic sensor 141 (e.g., a SONAR sensor), as described in, for example, WO 2018/050913 and WO 2020/104465, each of which is hereby incorporated by reference herein in its entirety. In such implementations, the speaker 142 generates or emits sound waves at a predetermined interval and/or frequency, and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user or a bed partner of the user (such as bed partner 220 in FIG. 2). Based at least in part on the data from the microphone 140 and/or the speaker 142, the control system 110 can determine a location of the user and/or one or more of the sleep-related parameters described in herein, such as, for example, a respiration signal, a respiration rate, an inspiration amplitude, an expiration amplitude, an inspiration-expiration ratio, a number of events per hour, a pattern of events, a sleep stage, pressure settings of the respiratory therapy device 122, a mouth leak status, or any combination thereof. In this context, a SONAR sensor may be understood to concern an active acoustic sensing, such as by generating/transmitting ultrasound or low frequency ultrasound sensing signals (e.g., in a frequency range of about 17-23 kHz, 18-22 kHz, or 17-18 kHz, for example), through the air. Such a system may be considered in relation to WO 2018/050913 and WO 2020/104465 mentioned above. In some implementations, the speaker 142 is a bone conduction speaker. In some implementations, the one or more sensors 130 include (i) a first microphone that is the same or similar to the microphone 140, and is integrated into the acoustic sensor 141 and (ii) a second microphone that is the same as or similar to the microphone 140, but is separate and distinct from the first microphone that is integrated into the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user and/or one or more of the sleep-related parameters described herein. An RF receiver (either the RF receiver 146 and the RF transmitter 148 or another RF pair) can also be used for wireless communication between the control system 110, the respiratory therapy device 122, the one or more sensors 130, the user device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147 (e.g., a RADAR sensor). In some such implementations, the RF sensor 147 includes a control circuit. The specific format of the RF communication could be WiFi, Bluetooth, etc.

In some implementations, the RF sensor 147 is a part of a mesh system. One example of a mesh system is a WiFi mesh system, which can include mesh nodes, mesh router(s), and mesh gateway(s), each of which can be mobile/movable or fixed. In such implementations, the WiFi mesh system includes a WiFi router and/or a WiFi controller and one or more satellites (e.g., access points), each of which include an RF sensor that the is the same as, or similar to, the RF sensor 147. The WiFi router and satellites continuously communicate with one another using WiFi signals. The WiFi mesh system can be used to generate motion data based at least in part on changes in the WiFi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein. For example, the image data from the camera 150 can be used to identify a location of the user, to determine a time when the user enters the user's bed (such as bed 230 in FIG. 2), and to determine a time when the user exits the bed 230. The camera 150 can also be used to track eye movements, pupil dilation (if one or both of the user's eyes are open), blink rate, or any changes during REM sleep. The camera 150 can also be used to track the position of the user, which can impact the duration and/or severity of apneic episodes in users with positional obstructive sleep apnea.

The IR sensor 152 outputs infrared image data reproducible as one or more infrared images (e.g., still images, video images, or both) that can be stored in the memory device 114. The infrared data from the IR sensor 152 can be used to determine one or more sleep-related parameters during the sleep session, including a temperature of the user and/or movement of the user. The IR sensor 152 can also be used in conjunction with the camera 150 when measuring the presence, location, and/or movement of the user. The IR sensor 152 can detect infrared light having a wavelength between about 700 nm and about 1 mm, for example, while the camera 150 can detect visible light having a wavelength between about 380 nm and about 740 nm.

The IR sensor 152 outputs infrared image data reproducible as one or more infrared images (e.g., still images, video images, or both) that can be stored in the memory device 114. The infrared data from the IR sensor 152 can be used to determine one or more sleep-related parameters during the sleep session, including a temperature of the user and/or movement of the user. The IR sensor 152 can also be used in conjunction with the camera 150 when measuring the presence, location, and/or movement of the user. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user that can be used to determine one or more sleep-related parameters, such as, for example, a heart rate, a heart rate pattern, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user, embedded in clothing and/or fabric that is worn by the user, embedded in and/or coupled to the user interface 124 and/or its associated headgear (e.g., straps, etc.), etc.

The ECG sensor 156 outputs physiological data associated with electrical activity of the heart of the user. In some implementations, the ECG sensor 156 includes one or more electrodes that are positioned on or around a portion of the user during the sleep session. The physiological data from the ECG sensor 156 can be used, for example, to determine one or more of the sleep-related parameters described herein.

The EEG sensor 158 outputs physiological data associated with electrical activity of the brain of the user. In some implementations, the EEG sensor 158 includes one or more electrodes that are positioned on or around the scalp of the user during the sleep session. The physiological data from the EEG sensor 158 can be used, for example, to determine a sleep stage of the user at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user. The data output by the analyte sensor 174 can be stored in the memory device 114 and used by the control system 110 to determine the identity and concentration of any analytes in the user's breath. In some implementations, the analyte sensor 174 is positioned near a mouth of the user to detect analytes in breath exhaled from the user's mouth. For example, when the user interface 124 is a facial mask that covers the nose and mouth of the user, the analyte sensor 174 can be positioned within the facial mask to monitor the user mouth breathing. In other implementations, such as when the user interface 124 is a nasal mask or a nasal pillow mask, the analyte sensor 174 can be positioned near the nose of the user to detect analytes in breath exhaled through the user's nose. In still other implementations, the analyte sensor 174 can be positioned near the user's mouth when the user interface 124 is a nasal mask or a nasal pillow mask. In this implementation, the analyte sensor 174 can be used to detect whether any air is inadvertently leaking from the user's mouth. In some implementations, the analyte sensor 174 is a volatile organic compound (VOC) sensor that can be used to detect carbon-based chemicals or compounds, such as carbon dioxide. In some implementations, the analyte sensor 174 can also be used to detect whether the user is breathing through their nose or mouth. For example, if the data output by an analyte sensor 174 positioned near the mouth of the user or within the facial mask (in implementations where the user interface 124 is a facial mask) detects the presence of an analyte, the control system 110 can use this data as an indication that the user is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user's face, near the connection between the conduit 126 and the user interface 124, near the connection between the conduit 126 and the respiratory therapy device 122, etc.). Thus, in some implementations, the moisture sensor 176 can be coupled to or integrated into the user interface 124 or in the conduit 126 to monitor the humidity of the pressurized air from the respiratory therapy device 122. In other implementations, the moisture sensor 176 is placed near any area where moisture levels need to be monitored. The moisture sensor 176 can also be used to monitor the humidity of the ambient environment surrounding the user, for example the air inside the user's bedroom. The moisture sensor 176 can also be used to track the user's biometric response to environmental changes.

One or more LiDAR sensors 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor 178 may also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

While shown separately in FIG. 1, any combination of the one or more sensors 130 can be integrated in and/or coupled to any one or more of the components of the system 100, including the respiratory therapy device 122, the user interface 124, the conduit 126, the humidification tank 129, the control system 110, the user device 170, or any combination thereof. For example, the acoustic sensor 141 and/or the RF sensor 147 can be integrated in and/or coupled to the user device 170. In such implementations, the user device 170 can be considered a secondary device that generates additional or secondary data for use by the system 100 (e.g., the control system 110) according to some aspects of the present disclosure. In some implementations, the pressure sensor 132 and/or the flow rate sensor 134 are integrated into and/or coupled to the respiratory therapy device 122. In some implementations, at least one of the one or more sensors 130 is not coupled to the respiratory therapy device 122, the control system 110, or the user device 170, and is positioned generally adjacent to the user during the sleep session (e.g., positioned on or in contact with a portion of the user, worn by the user, coupled to or positioned on the nightstand, coupled to the mattress, coupled to the ceiling, etc.). More generally, the one or more sensors 130 can be positioned at any suitable location relative to the user such that the one or more sensors 130 can generate physiological data associated with the user and/or the bed partner 220 during one or more sleep session.

The data from the one or more sensors 130 can be analyzed to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, an average duration of events, a range of event durations, a ratio between the number of different events, a sleep stage, an apnea-hypopnea index (AHI), or any combination thereof. The one or more events can include snoring, apneas, central apneas, obstructive apneas, mixed apneas, hypopneas, an intentional user interface leak, an unintentional user interface leak, a mouth leak, a cough, a restless leg, a sleeping disorder, choking, an increased heart rate, labored breathing, an asthma attack, an epileptic episode, a seizure, increased blood pressure, hyperventilation, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 130, or from other types of data.

The user device 170 includes a display device 172. The user device 170 can be, for example, a mobile device such as a smart phone, a tablet, a laptop, a gaming console, a smart watch, or the like. Alternatively, the user device 170 can be an external sensing system, a television (e.g., a smart television) or another smart home device (e.g., a smart speaker(s) such as Google Home, Amazon Echo, Alexa etc.). In some implementations, the user device 170 is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices 170 can be used by and/or included in the system 100.

The blood pressure device 180 is generally used to aid in generating physiological data for determining one or more blood pressure measurements associated with a user. The blood pressure device 180 can include at least one of the one or more sensors 130 to measure, for example, a systolic blood pressure component and/or a diastolic blood pressure component.

In some implementations, the blood pressure device 180 is a sphygmomanometer including an inflatable cuff that can be worn by a user and a pressure sensor (e.g., the pressure sensor 132 described herein). For example, as shown in the example of FIG. 2, the blood pressure device 180 can be worn on an upper arm of the user. In such implementations where the blood pressure device 180 is a sphygmomanometer, the blood pressure device 180 also includes a pump (e.g., a manually operated bulb) for inflating the cuff. In some implementations, the blood pressure device 180 is coupled to the respiratory therapy device 122 of the respiratory therapy system 120, which in turn delivers pressurized air to inflate the cuff. More generally, the blood pressure device 180 can be communicatively coupled with, and/or physically integrated in (e.g., within a housing), the control system 110, the memory device 114, the respiratory therapy system 120, the user device 170, and/or the activity tracker 190.

The activity tracker 190 is generally used to aid in generating physiological data for determining an activity measurement associated with the user. The activity measurement can include, for example, a number of steps, a distance traveled, a number of steps climbed, a duration of physical activity, a type of physical activity, an intensity of physical activity, time spent standing, a respiration rate, an average respiration rate, a resting respiration rate, a maximum respiration rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. The activity tracker 190 includes one or more of the sensors 130 described herein, such as, for example, the motion sensor 138 (e.g., one or more accelerometers and/or gyroscopes), the PPG sensor 154, and/or the ECG sensor 156.

In some implementations, the activity tracker 190 is a wearable device that can be worn by the user, such as a smartwatch, a wristband, a ring, or a patch. For example, referring to FIG. 2, the activity tracker 190 is worn on a wrist of the user. The activity tracker 190 can also be coupled to or integrated a garment or clothing that is worn by the user. Alternatively, still, the activity tracker 190 can also be coupled to or integrated in (e.g., within the same housing) the user device 170. More generally, the activity tracker 190 can be communicatively coupled with, or physically integrated in (e.g., within a housing), the control system 110, the memory device 114, the respiratory therapy system 120, the user device 170, and/or the blood pressure device 180.

While the control system 110 and the memory device 114 are described and shown in FIG. 1 as being a separate and distinct component of the system 100, in some implementations, the control system 110 and/or the memory device 114 are integrated in the user device 170 and/or the respiratory therapy device 122. Alternatively, in some implementations, the control system 110 or a portion thereof (e.g., the processor 112) can be located in a cloud (e.g., integrated in a server, integrated in an Internet of Things (IOT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system for identifying a user interface used by a user, according to implementations of the present disclosure. For example, a first alternative system includes the control system 110, the memory device 114, and at least one of the one or more sensors 130. As another example, a second alternative system includes the control system 110, the memory device 114, at least one of the one or more sensors 130, and the user device 170. As yet another example, a third alternative system includes the control system 110, the memory device 114, the respiratory therapy system 120, at least one of the one or more sensors 130, and the user device 170. As a further example, a fourth alternative system includes the control system 110, the memory device 114, the respiratory therapy system 120, at least one of the one or more sensors 130, the user device 170, and the blood pressure device 180 and/or activity tracker 190. Thus, various systems for modifying pressure settings can be formed using any portion or portions of the components shown and described herein and/or in combination with one or more other components.

Referring again to FIG. 2, in some implementations, the control system 110, the memory device 114, any of the one or more sensors 130, or a combination thereof can be located on and/or in any surface and/or structure that is generally adjacent to the bed 230 and/or the user 210. For example, in some implementations, at least one of the one or more sensors 130 can be located at a first position on and/or in one or more components of the respiratory therapy system 120 adjacent to the bed 230 and/or the user 210. The one or more sensors 130 can be coupled to the respiratory therapy system 120, the user interface 124, the conduit 126, the display device 128, the humidification tank 129, or a combination thereof.

Alternatively, or additionally, at least one of the one or more sensors 130 can be located at a second position on and/or in the bed 230 (e.g., the one or more sensors 130 are coupled to and/or integrated in the bed 230). Further, alternatively or additionally, at least one of the one or more sensors 130 can be located at a third position on and/or in the mattress 232 that is adjacent to the bed 230 and/or the user 210 (e.g., the one or more sensors 130 are coupled to and/or integrated in the mattress 232). Alternatively, or additionally, at least one of the one or more sensors 130 can be located at a fourth position on and/or in a pillow that is generally adjacent to the bed 230 and/or the user 210.

Alternatively, or additionally, at least one of the one or more sensors 130 can be located at a fifth position on and/or in the nightstand 240 that is generally adjacent to the bed 230 and/or the user 210. Alternatively, or additionally, at least one of the one or more sensors 130 can be located at a sixth position such that the at least one of the one or more sensors 130 are coupled to and/or positioned on the user 210 (e.g., the one or more sensors 130 are embedded in or coupled to fabric, clothing, and/or a smart device worn by the user 210). More generally, at least one of the one or more sensors 130 can be positioned at any suitable location relative to the user 210 such that the one or more sensors 130 can generate sensor data associated with the user 210.

In some implementations, a primary sensor, such as the microphone 140, is configured to generate acoustic data associated with the user 210 during a sleep session. For example, one or more microphones (the same as, or similar to, the microphone 140 of FIG. 1) can be integrated in and/or coupled to (i) a circuit board of the respiratory therapy device 122, (ii) the conduit 126, (iii) a connector between components of the respiratory therapy system 120, (iv) the user interface 124, (v) a headgear (e.g., straps) associated with the user interface, or (vi) a combination thereof.

In some implementations, one or more secondary sensors may be used in addition to the primary sensor to generate additional data. In some such implementations, the one or more secondary sensors include: a microphone (e.g., the microphone 140 of the system 100), a flow rate sensor (e.g., the flow rate sensor 134 of the system 100), a pressure sensor (e.g., the pressure sensor 132 of the system 100), a temperature sensor (e.g., the temperature sensor 136 of the system 100), a camera (e.g., the camera 150 of the system 100), a vane sensor (VAF), a hot wire sensor (MAF), a cold wire sensor, a laminar flow sensor, an ultrasonic sensor, an inertial sensor, or a combination thereof.

Additionally, or alternatively, one or more microphones (the same as, or similar to, the microphone 140 of FIG. 1) can be integrated in and/or coupled to a co-located smart device, such as the user device 170, a TV, a watch (e.g., a mechanical watch or another smart device worn by the user), a pendant, the mattress 232, the bed 230, beddings positioned on the bed 230, the pillow, a speaker (e.g., the speaker 142 of FIG. 1), a radio, a tablet device, a waterless humidifier, or a combination thereof. A co-located smart device can be any smart device that is within range for detecting sounds emitted by the user, the respiratory therapy system 120, and/or any portion of the system 100. In some implementations, the co-located smart device is a smart device that is in the same room as the user during the sleep session.

Additionally, or alternatively, in some implementations, one or more microphones (the same as, or similar to, the microphone 140 of FIG. 1) can be remote from the system 100 (FIG. 1) and/or the user 210 (FIG. 2), so long as there is an air passage allowing acoustic signals to travel to the one or more microphones. For example, the one or more microphones can be in a different room from the room containing the system 100.

As used herein, a sleep session can be defined in a number of ways based at least in part on, for example, an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 172 of the user device 170 (FIG. 1) to manually initiate or terminate the sleep session.

Figure 3:
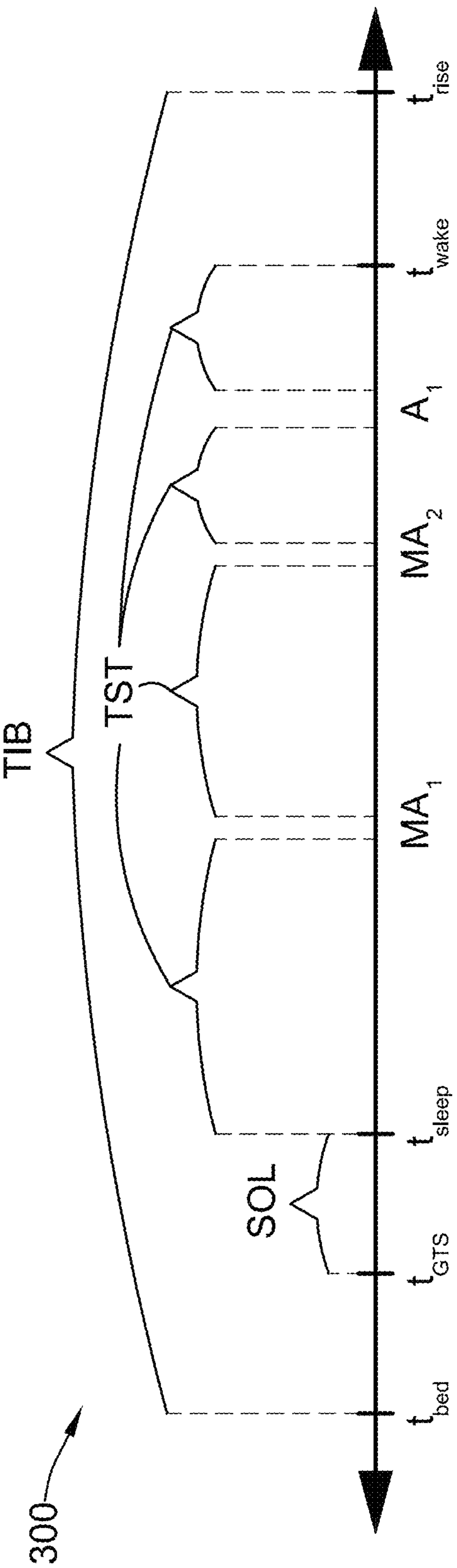
FIG. 3 illustrates an exemplary timeline for a sleep session, according to some implementations of the present disclosure.

Referring to FIG. 3, an exemplary timeline 300 for a sleep session is illustrated. The timeline 300 includes an enter bed time ($t_{bed}$), a go-to-sleep time ($t_{GTS}$), an initial sleep time ($t_{sleep}$), a first micro-awakening $MA_1$, a second micro-awakening $MA_2$, an awakening A, a wake-up time ($t_{wake}$), and a rising time ($t_{rise}$).

The enter bed time $t_{bed}$ is associated with the time that the user initially enters the bed (e.g., bed 230 in FIG. 2) prior to falling asleep (e.g., when the user lies down or sits in the bed). The enter bed time $t_{bed}$ can be identified based at least in part on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time thed can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 170, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based at least in part on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based at least in part on a rise threshold duration (e.g., the user has left the bed for at least 15 minutes, at least 20 minutes, at least 30 minutes, at least 1 hour, etc.). The enter bed time thed time for a second, subsequent sleep session can also be defined based at least in part on a rise threshold duration (e.g., the user has left the bed for at least 4 hours, at least 6 hours, at least 8 hours, at least 12 hours, etc.).

As described above, the user may wake up and get out of bed one more times during the night between the initial thed and the final $t_{rise}$. In some implementations, the final wake-up time $t_{wake}$ and/or the final rising time $t_{rise}$ that are identified or determined based at least in part on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based at least in part on the system monitoring the user's sleep behavior.

The total time in bed (TIB) is the duration of time between the time enter bed time thed and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 300 of FIG. 3, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 4:
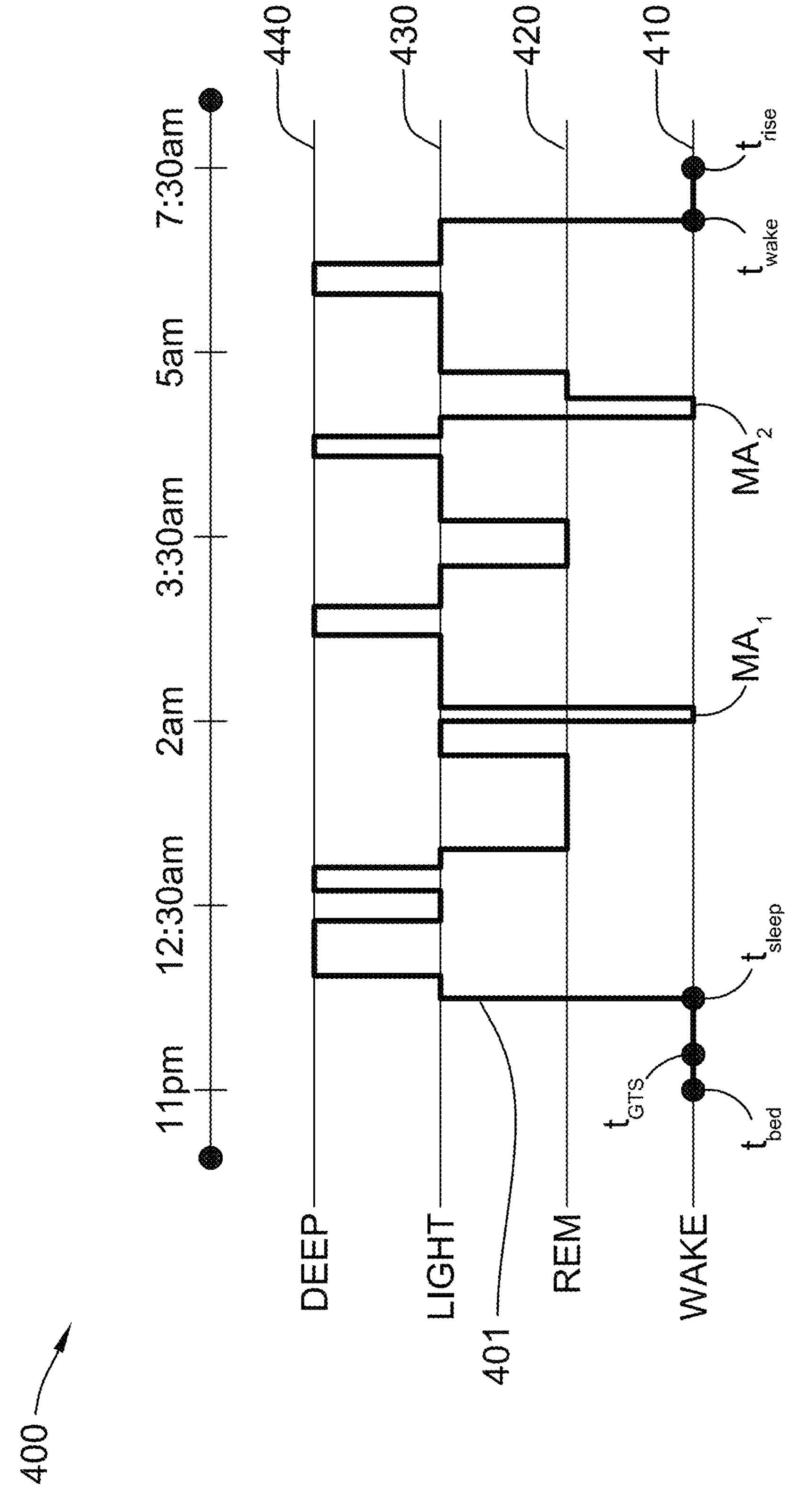
FIG. 4 illustrates an exemplary hypnogram associated with the sleep session of FIG. 3, according to some implementations of the present disclosure.

Referring to FIG. 4, an exemplary hypnogram 400 corresponding to the timeline 300 (FIG. 3), according to some implementations, is illustrated. As shown, the hypnogram 400 includes a sleep-wake signal 401, a wakefulness stage axis 410, a REM stage axis 420, a light sleep stage axis 430, and a deep sleep stage axis 440. The intersection between the sleep-wake signal 401 and one of the axes 410-440 is indicative of the sleep stage at any given time during the sleep session.

The sleep-wake signal 401 can be generated based at least in part on physiological data associated with the user (e.g., generated by one or more of the sensors 130 described herein). The sleep-wake signal can be indicative of one or more sleep stages, including wakefulness, relaxed wakefulness, microawakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 400 is shown in FIG. 4 as including the light sleep stage axis 430 and the deep sleep stage axis 440, in some implementations, the hypnogram 400 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration amplitude ratio, an inspiration-expiration duration ratio, a number of events per hour, a pattern of events, or any combination thereof. Information describing the sleep-wake signal can be stored in the memory device 114.

The hypnogram 400 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 4), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based at least in part on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 130 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time $t_{bed}$ can be determined based at least in part on, for example, data generated by the motion sensor 138, the microphone 140, the camera 150, or any combination thereof. The go-to-sleep time can be determined based at least in part on, for example, data from the motion sensor 138 (e.g., data indicative of no movement by the user), data from the camera 150 (e.g., data indicative of no movement by the user and/or that the user has turned off the lights), data from the microphone 140 (e.g., data indicative of the using turning off a TV), data from the user device 170 (e.g., data indicative of the user no longer using the user device 170), data from the pressure sensor 132 and/or the flow rate sensor 134 (e.g., data indicative of the user turning on the respiratory therapy device 122, data indicative of the user donning the user interface 124, etc.), or any combination thereof.

Figure 5:
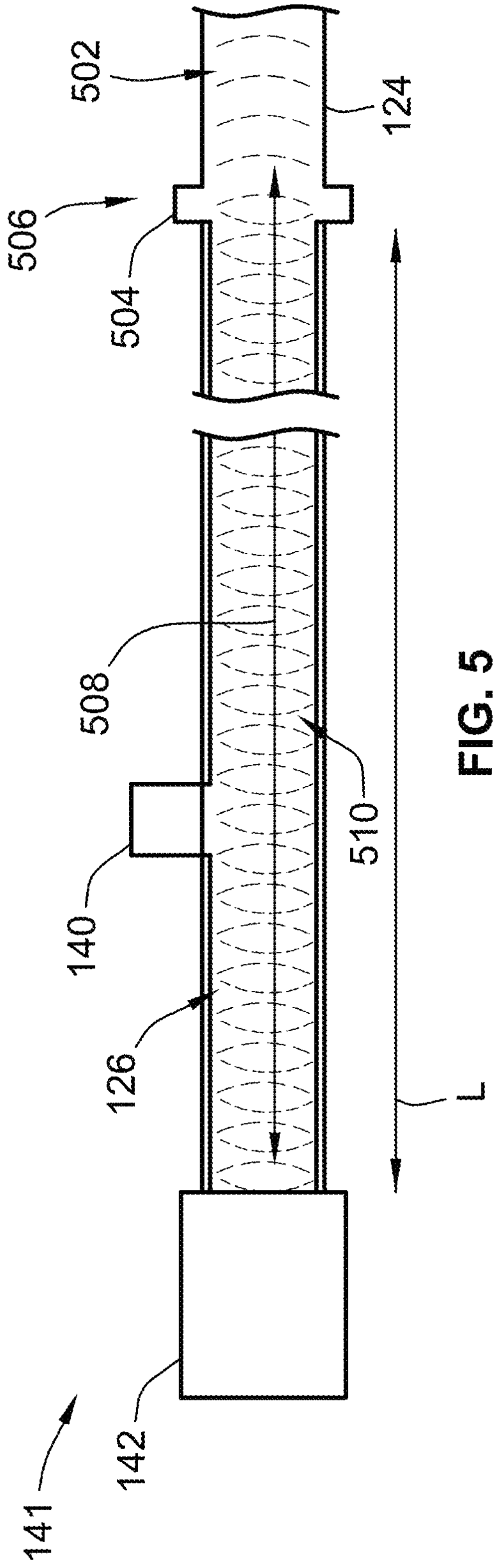
FIG. 5 illustrates the generation of acoustic data in response to an acoustic reflection indicative of one or more features of a user interface, according to some implementations of the present disclosure.

FIG. 5 illustrates the generation of acoustic data in response to an acoustic reflection indicative of one or more features of a user interface, according to aspects of the present disclosure. The generation of the acoustic data includes the acoustic sensor 141, which includes the microphone 140 (or any type of audio transducer) and a speaker 142. However, as discussed above, the speaker 142 can instead be replaced by another device that can generate an acoustic signal, such as the motor of the respiratory therapy device 122. The microphone 140 and speaker 142 are shown in specific locations relative to the conduit 126, which is connected to the respiratory therapy device 122 (not shown). However, the locations of the microphone 140 and the speaker 142 can vary from what is shown, as discussed above.

The speaker 142 emits an acoustic signal 502 within the conduit 126. The acoustic signal 502 is in the form of a sound. The sound can be one or more of a standard sound (e.g., an original, unmodified sound from an off-the-shelf sound application), a custom sound, an inaudible frequency, a white noise sound, a broad band impulse, a continuous sinusoidal waveform, a square waveform, a sawtooth waveform, and a frequency modulated sinusoid (e.g., chirp). According to some other implementations, the acoustic signal 502 can be in the form of one or more of an audible sound or an ultrasonic sound. According to some other implementations, the acoustic signal 502 is in the form of an inaudible sound, where the sound is inaudible based on one or both of the frequency of the sound (e.g., the frequency being outside of the frequency range for human hearing) or the amplitude of the sound (e.g., the amplitude being low enough that the sound is not loud enough for human perception).

In one or more implementations, the acoustic signal 502 is emitted at specific times, such as when the user first puts on the user interface, after the user takes off the user interface, after detecting that an apnea event or a hypopnea event is occurring (e.g., after detecting using a respiratory therapy device that an apnea event or a hypopnea event is occurring). For example, the specific monitoring times are selected to be at intervals of 0.1 seconds for a duration of at least 4 seconds.

The acoustic signal 502 travels down the length L of the conduit 126 until the acoustic signal 502 contacts a feature 504 of the user interface 124 at or near a connection 506 of the user interface 124 with the conduit 126. The feature 504 can include a widening (or a narrowing) of the pathway 508 formed through the conduit 126 and the user interface 124. The widening at the feature 504 causes a change in the acoustic impedance of the acoustic signal 502 and an acoustic reflection 510. The acoustic reflection 510 travels back down the length L of the conduit 126 until it reaches the microphone 140. The microphone 140 detects the acoustic reflection 510 and generates acoustic data in response to the acoustic reflection 510. The generated acoustic data is subsequently analyzed for categorizing and/or characterizing the user interface, as further discussed below with respect to FIG. 7.

The acoustic signal 502 can continue beyond the feature 504 and into the user interface 124. Although not illustrated, the user interface 124 can include one or more additional features that change the acoustic impedance of the acoustic signal 502, which further generates the acoustic reflection 510. Thus, although only the feature 504 is illustrated and described as causing the acoustic reflection 510, there can be multiple features of the user interface 124 that can all contribute to the acoustic reflection 510.

As such, in some implementations, the system 100 is configured to generate acoustic data, which is in turn analyzed by the control system 110. In some implementations, the acoustic data includes reflected sound waves received by a microphone (e.g., the microphone 140 of the system 100) that are transmitted from a speaker (e.g., the speaker 142 of the system 100, or an external speaker). The reflected sound waves are indicative of shapes and dimensions of the components in the sound waves' path(s). Additionally or alternatively, the acoustic data includes sound(s) from the user that is indicative of one or more sleep-related parameters (e.g., breathing through the nose, breathing through the mouth, snoring, sniffling).

For example, the acoustic data can include data generated by the microphone 140. The speaker 142 generates a sound. The sound can travel through the humidification tank 129, along a first connection, along the conduit 126, via a second connection, via a waterless humidifier (if fitted), to one or more mask cavities (e.g., nostrils and/or mouth), to the user's respiratory therapy system (including nose and/or mouth, airway(s), lungs, etc.). For each change in the path (e.g., a cavity, a junction, a change in shape), a reflection at that point based on speed of sound is seen. The different types and distances of reflection(s) can be used to define a type and/or a model of user interface 124.

In some implementations, a cepstrum analysis is implemented to analyze the acoustic data. Cepstrum is a "quefrency" domain, which is also known as the spectrum of the log of a time domain waveform. For example, a cepstrum may be considered the inverse Fourier Transform of the log spectrum of the forward Fourier Transform of the decibel spectrum, etc. The operation essentially can convert a convolution of an impulse response function (IRF) and a sound source into an addition operation so that the sound source may then be more easily accounted for or removed so as to isolate data of the IRF for analysis. Techniques of cepstrum analysis are described in detail in a scientific paper entitled "The Cepstrum: A Guide to Processing" (Childers et al, Proceedings of the IEEE, Vol. 65, No. 10, October 1977) and Randall R B, Frequency Analysis, Copenhagen: Bruel & Kjaer, p. 344 (1977, revised ed. 1987), which is hereby incorporated by reference herein in its entirety.

Such a method may be understood in terms of the property of convolution. The convolution of f and g can be written as $f*g$. This operation can be the integral of the product of the two functions (f and g) after one is reversed and shifted. As such, it is a type of integral transform as Equation 1, as follows:

$$(f*g)(t) \stackrel{def}{=} \int_{-\infty}^{\infty} f(\tau)\cdot g(t-\tau)d\tau \quad \text{Eq. 1}$$

While the symbol t is used above, it need not represent the time domain. But, in that context, the convolution formula can be described as a weighted average of the function f(τ) at the moment t where the weighting is given by g(−τ) simply shifted by amount t. As t changes, the weighting function emphasizes different parts of the input function.

More generally, if f and g are complex-valued functions on $R^d$, then their convolution may be defined as the integral of Equation 2:

$$(f*g))(x)=\int_{R^d} f(y)g(x-y)dy=\int_{R^d} f(x-y)g(y)dy \quad \text{Eq. 2}$$

A mathematical model that can relate an acoustic system output to the input for a time-invariant linear system, such as one involving conduits of a respiratory treatment apparatus, (which may include some human or other unknown part of the system) can be based on this convolution. The output measured at a microphone of the system may be considered as the input noise "convolved" with the system Impulse Response Function (IRF) as a function of time (t), as shown in Equation 3:

$$y(t)=s_1(t)*h_1(t) \quad \text{Eq. 3}$$

where * denotes the convolution function; y(t) is the signal measured at the sound sensor; $S_1(t)$ is the sound or noise source such, as a noise or sound created in or by a flow generator of a respiratory treatment apparatus; and $h_1(t)$ is the system IRF from the noise or sound source to the sound sensor. The Impulse Response Function (IRF) is the system response to a unit impulse input.

Conversion of Equation 3 into the frequency domain by means of the Fourier Transform of the measured sound data (e.g., a discrete Fourier Transform ("DFT") or a fast Fourier transform ("FFT") and considering the Convolution Theorem, Equation 4 is produced:

$$y(t) = s_1(t) * h_1(t) \xrightarrow{\text{Fourier Transform}} Y(f) = S_1(f)H_1(f) \quad \text{Eq. 4}$$

where Y(f) is the Fourier Transform of y(t); $S_1(f)$ is the Fourier Transform of $s_1(t)$; and $H_1(f)$ is the Fourier Transform of $h_1(t)$. In such a case, convolution in the time domain becomes a multiplication in the frequency domain.

A logarithm of Equation 4 may be applied so that the multiplication is converted into an addition, resulting in Equation 5:

$$\text{Log}\{Y(f)\}=\text{Log}\{S_1(f)H_1(f)\}=\text{Log}\{S_1(f)\}+\text{Log}\{H_1(f)\} \quad \text{Eq. 5}$$

Equation 5 may then be converted back into the time domain, by an Inverse Fourier Transform (IFT) (e.g., an inverse DFT or inverse FFT), which results in a complex cepstrum (K(τ)) (complex because one can work from the complex spectrum)—the inverse Fourier Transform of the logarithm of the spectrum; Equation 6.

$$K(\tau)=\text{IFT}[\text{Log}\{S_1(f)\}+\text{Log}\{H_1(f)\}] \quad \text{Eq. 6}$$

where "τ" is a real valued variable known as quefrency, with units measured in seconds. From this, the effects that are convolutive in the time domain become additive in the logarithm of the spectrum, and remain so in the cepstrum.

Consideration of the data from a cepstrum analysis, such as examining the data values of the quefrency, may provide information about the system. For example, by comparing cepstrum data of a system from a prior or known baseline of cepstrum data for the system, the comparison, such as a difference, can be used to recognize differences or similarities in the system that may then be used to implement varying functions or purposes disclosed herein. The following disclosure can utilize the methodologies of such an analysis, as herein explained, to implement the identification of the user interface.

Therefore, in some implementations, analysis of the acoustic data using cepstrum can be used to measure the cross-sectional area, and change(s) in the cross-sectional area of the user interface 124, the nasal passages, the estimated dimensions of sinuses. The changes in the nasal passages and the estimated dimensions of the sinuses may be indicative of inflammation and/or congestion.

In some implementations, direct spectral methods can be implemented to analyze the acoustic data. Some examples of direct spectral methods include processing discrete Fourier transform (DFT), fast Fourier transform (FFT) with a sliding window, short time Fourier transform (STFT), wavelets, wavelet-based cepstrum calculation, deep neural networks (e.g., using imaging methods applied to spectrograms), Hilbert-Huang transform (HHT), empirical mode decomposition (EMD), blind source separation (BSS), Kalman filters, or a combination thereof. In some implementations, cepstral coefficients (CCs) such as mel-frequency cepstral coefficients (MFCCs) may be used, for example, by treating the acoustic data analysis as a speech recognition problem and using a machine learning/classification system.

In some implementations, the system of the present disclosure includes a flow rate sensor (e.g., the flow rate sensor 134 of FIG. 1) and/or a pressure sensor (e.g., the pressure sensor 132 of FIG. 1). The flow rate sensor 134 can be used to generate flow data associated with the user 210 (FIG. 2) of the respiratory therapy device 122 during the sleep session. Examples of flow sensors (such as, for example, the flow rate sensor 134) are described in International Publication No. WO 2012/012835, which is hereby incorporated by reference herein in its entirety. In some implementations, the flow rate sensor 134 is configured to measure a vent flow (e.g., intentional "leak"), an unintentional leak (e.g., mouth leak (e.g., a leak from the mouth when using a nasal mask or a nasal pillow mask) and/or mask leak), a patient flow (e.g., air into and/or out of lungs), or a combination thereof. In some implementations, the flow data can be analyzed to determine cardiogenic oscillations of the user.

Figure 6A:
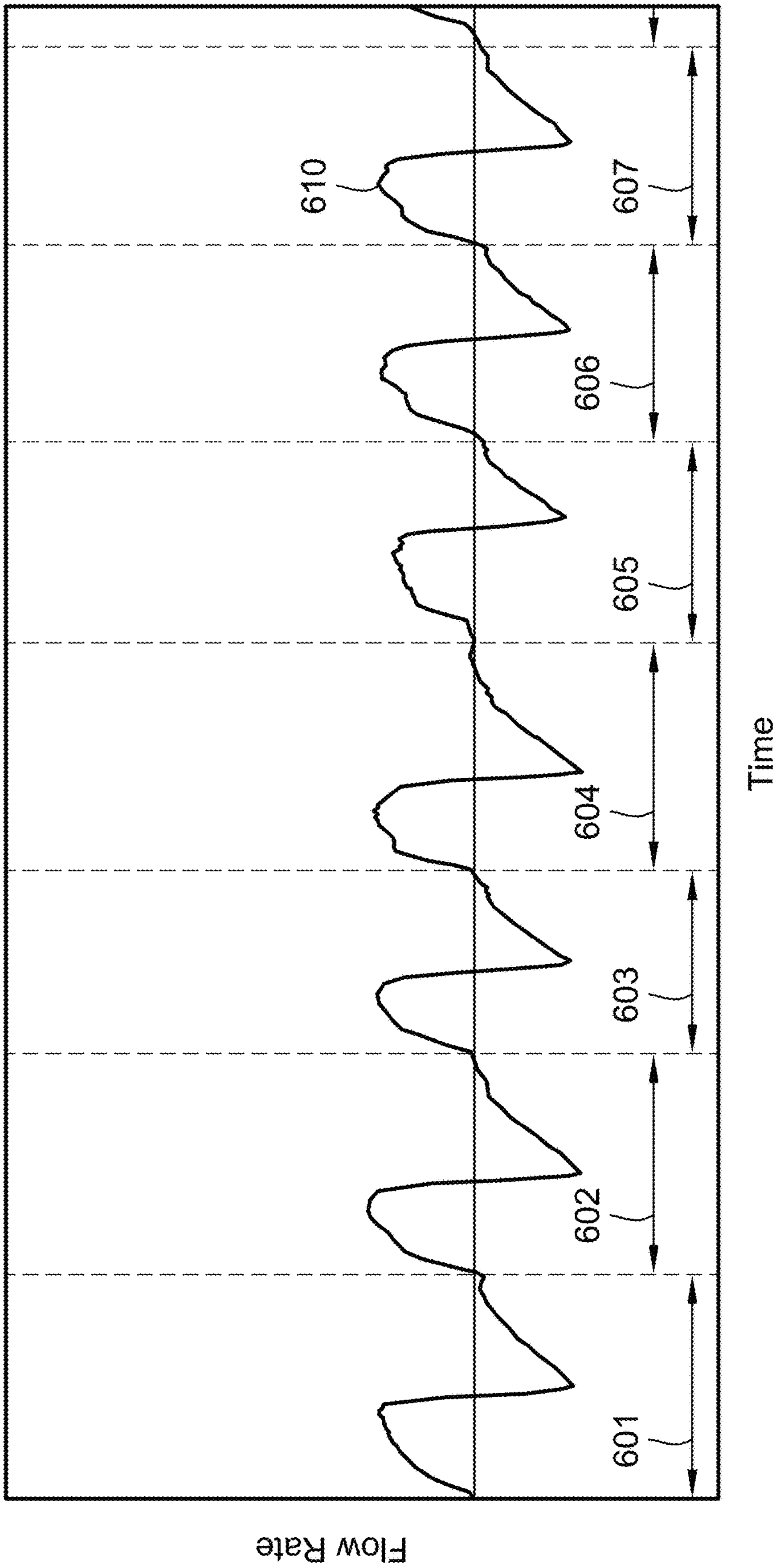
FIG. 6A illustrates flow data associated with a user of a respiratory therapy system, according to some implementations of the present disclosure.

In some implementations, the flow rate sensor and/or a pressure sensor is configured to generate flow data over a period of therapy time. For example, FIG. 6A illustrates a portion of such flow data associated with a user (e.g., the user 210 of FIG. 2) of a respiratory therapy system (e.g., the respiratory therapy system 120 of FIG. 1), according to some implementations of the present disclosure. As shown in FIG. 6A, a plurality of flow rate values measured over about seven full breathing cycles (601-607) is plotted as a continuous curve 610.

Figure 6B:
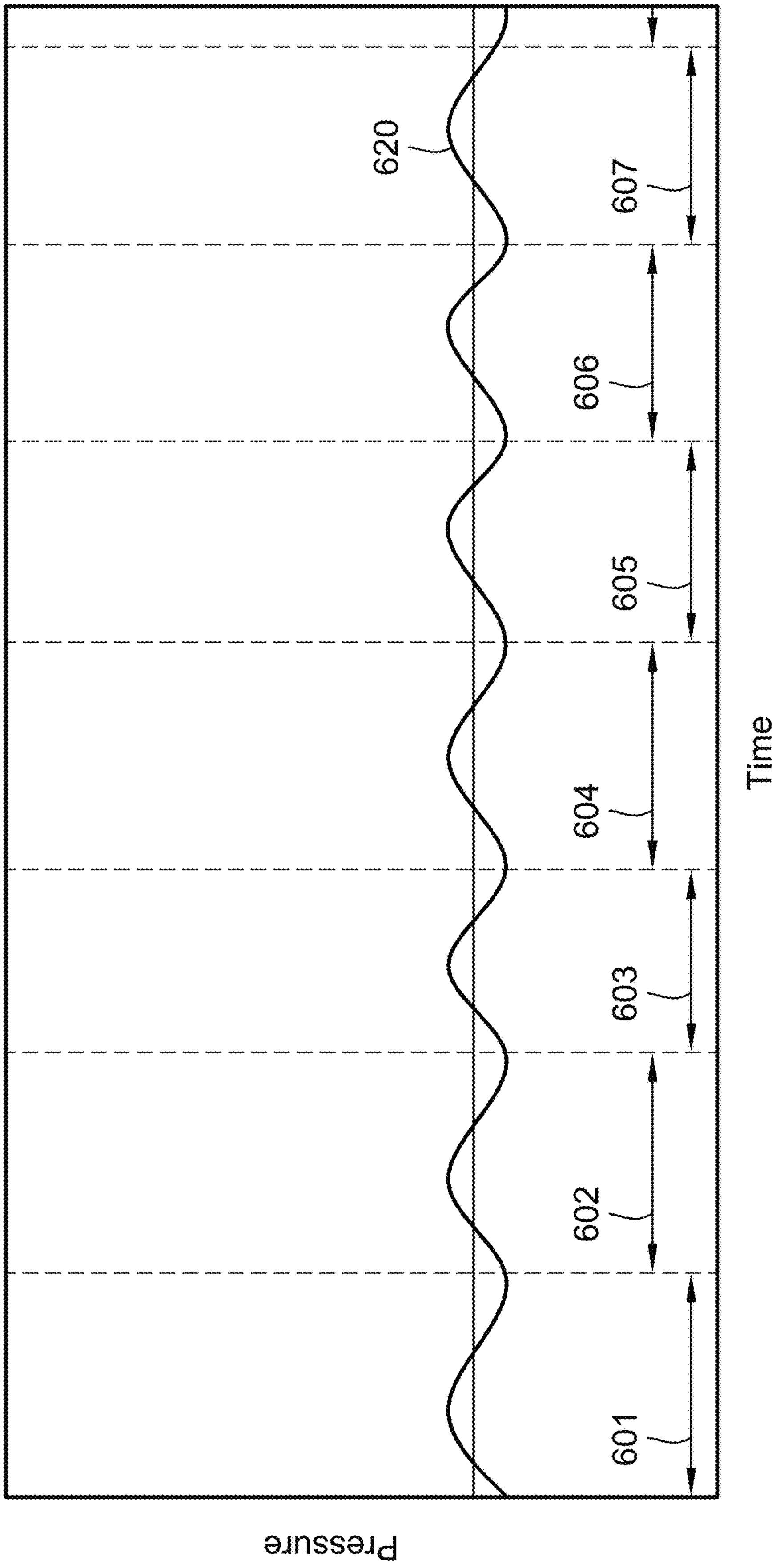
FIG. 6B illustrates pressure data associated with a user of a continuous positive airway pressure system, according to some implementations of the present disclosure.

In some implementations, the pressure sensor is configured to generate pressure data over a period of therapy time. For example, FIG. 6B illustrates pressure data associated with a user of a CPAP system, according to some implementations of the present disclosure. The pressure data shown in FIG. 6B was generated over the same period of therapy time as that of FIG. 6A. As shown in FIG. 6B, a plurality of pressure values measured over about seven full breathing cycles (601-607) is plotted as a continuous curve 620. Because a CPAP system is used, the continuous pressure curve of FIG. 6B exhibits a generally sinusoidal pattern with a relatively small amplitude, because the CPAP system attempts to maintain the constant predetermined air pressure for the system during the seven full breathing cycles.

Figure 6C:
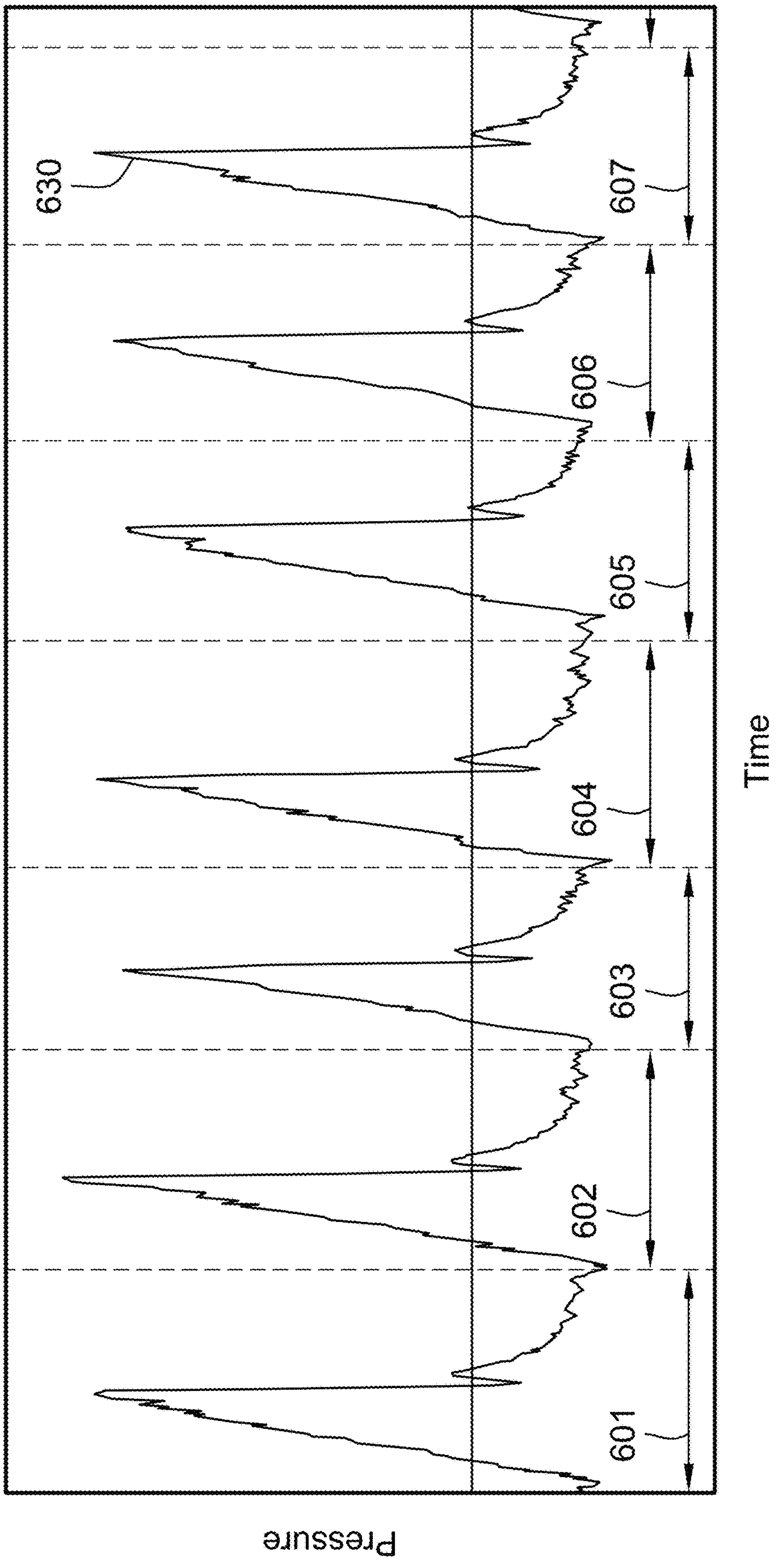
FIG. 6C illustrates pressure data associated with a user of a respiratory therapy system with an expiratory pressure relief module, according to some implementations of the present disclosure.

Referring to FIG. 6C, pressure data associated with a user of a respiratory therapy system with an expiratory pressure relief (EPR) module is illustrated, according to some implementations of the present disclosure. The pressure data shown in FIG. 6C was generated over the same period of therapy time as that of FIG. 6A. As shown in FIG. 6C, a plurality of pressure values measured over about seven full breathing cycles (601-607) is plotted as a continuous curve 630. The continuous curve 630 of FIG. 6C is different from the continuous curve 620 of FIG. 6B, because the EPR (Expository Pressure Relief) module (used for the pressure data in FIG. 6C) can have different settings for an EPR level, which is associated with a difference between a pressure level during inspiration and a reduced pressure level during expiration.

Figure 7:
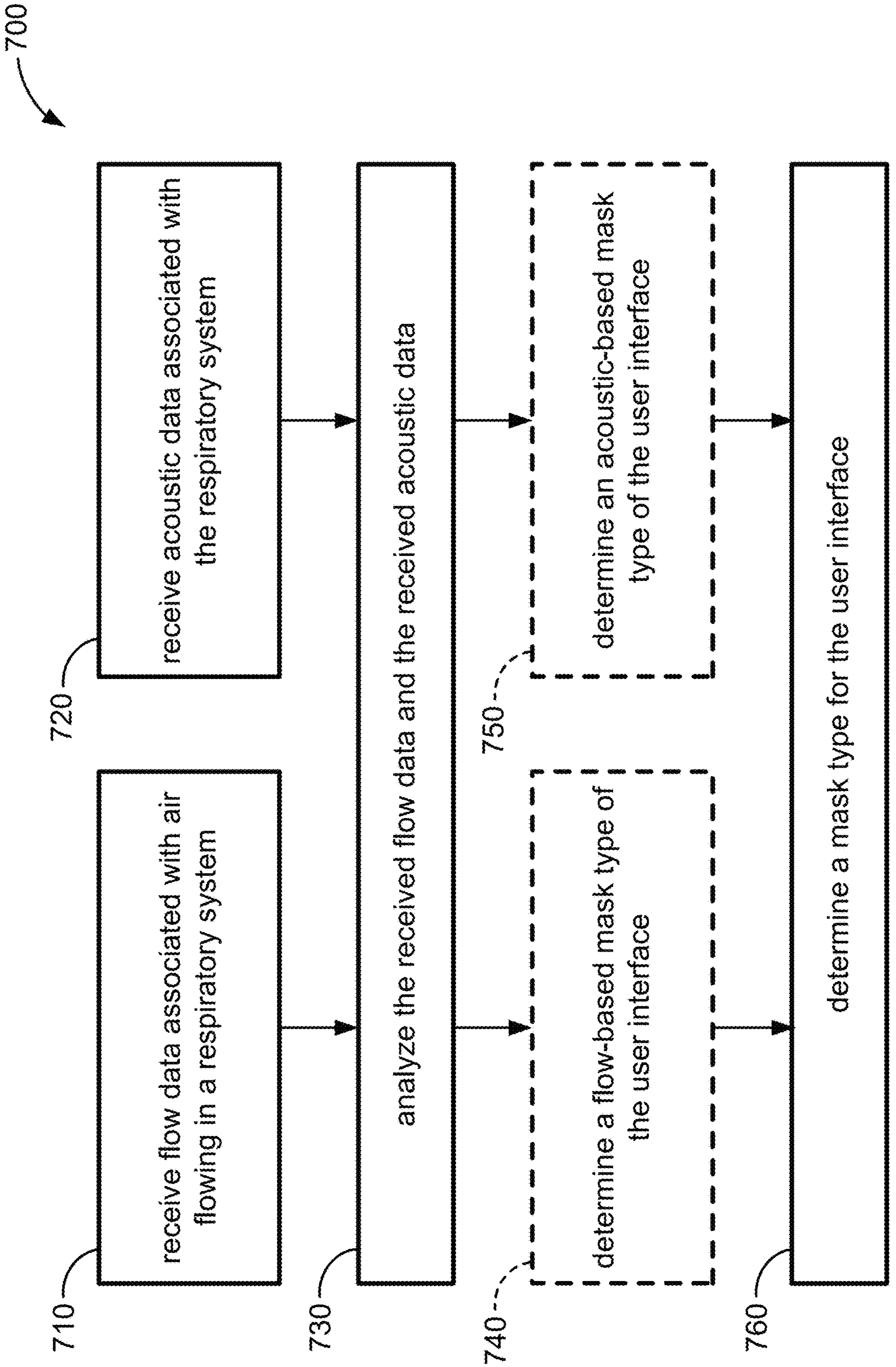
FIG. 7 is a flow diagram for a method for identifying a user interface, according to some implementations of the present disclosure.

Referring to FIG. 7, a flow diagram for a method 700 for identifying a user interface is disclosed. Generally, method 700 can be used to characterize the type of vent that the user interface has, in order to categorize the user interface as a specific type that is known to have that vent. One or more steps of the method 700 can be implemented using any element or aspect of the system 100 (FIGS. 1-2) described herein. At step 710, flow data associated with air flowing in a respiratory therapy system is received. The flow data can include flow rate data and/or pressure data. The flow data can be generated using one or more sensors 130 of the system 100, such as the flow rate sensor 134 and/or the pressure sensor 132.

At step 720, acoustic data associated with the respiratory therapy system is received. The acoustic data can be generated using one or more sensors 130 of the system 100, such as the microphone 140 and/or the speaker 142. As discussed herein, the microphone 140 can be external to the respiratory therapy system. Additionally or alternatively, the microphone 140 can be coupled to a smart device, a smart phone, a smart speaker, or any combination thereof. Additionally or alternatively, the microphone 140 can be an integrated microphone coupled to (i) a conduit of a respiratory therapy device of the respiratory therapy system, (ii) a circuit board of the respiratory therapy device of the respiratory therapy system, (iii) a connector of the respiratory therapy system, (iv) the user interface of the respiratory therapy system, or (v) any other component of the respiratory therapy system.

In some implementations, the flow data received at step 710 and the acoustic data received at step 720 are received when the user is wearing the user interface during the sleep session. In other implementations, the flow data and the acoustic data are received when the user is not wearing the user interface. In further implementations, the flow data and the acoustic data are received during a dedicated period of time, which may be prior to the beginning of the sleep session, or at the beginning of the sleep session before the user falls asleep. During this dedicated period of time, the user may be wearing the user interface, not wearing the user interface, or wearing the user interface for a first set of one or more portions and not wearing the user interface for a second set of one or more portions. The collection of the flow data and the acoustic data can be initiated in response to receiving instructions and/or input from the user.

At step 730, the received flow data and the received acoustic data are analyzed. In some implementations, the analyzed acoustic data includes Cepstrum data and/or an acoustic spectral signature as discussed above with reference to FIG. 5. In some such implementations, analyzing the received acoustic data includes a Cepstrum analysis, an autocepstrum analysis, an auto-correlation analysis, a spectral analysis, or a combination thereof. The spectral analysis can include a fast Fourier transform (FFT) with a sliding window, a spectrogram, a short time Fourier transform (STFT), a wavelet-based analysis, or a combination thereof.

Further, in some implementations, the analyzing the received flow data and the received acoustic data (step 730) includes processing the received flow data (step 710) and/or the received acoustic data (step 720) to identify one or more features. The features can include a maximum magnitude of the cepstrum, a minimum magnitude of the cepstrum, a standard deviation of the cepstrum, a skewness of the cepstrum, a kurtosis of the cepstrum, a median of an absolute value of the cepstrum, a sum of the absolute value of the cepstrum, a sum of a positive area of the cepstrum, a sum of a negative area of the cepstrum, a fundamental frequency, an energy corresponding to the fundamental frequency, a mean energy, at least one resonant frequency of a combination of the conduit and the user interface, a change in the at least one resonant frequency, a number of peaks within a range, a peak prominence, a distance between peaks, one or more spectral signatures, one or more frequencies, one or more amplitudes, one or more pressure values, one or more flow rate values, one or more ratios of pressure values to flow rate values, or any combination or change in thereof. Any features involving changes may include changes relative to previously-determined features, changes relative to a library of known mask-specific features, or changes relative to other baseline values.

At step 760, a mask type for the user interface is determined based at least in part on the analysis. For example, in some implementations, the mask type for the user interface includes a mask family, such as (i) full face, (ii) partial face, (iii) nasal, and (iv) nasal pillows. In some implementations, the mask type could also include a total-face mask, which may cover, in addition to the user's mouth and nose, some or all of the user's eyes and/or ears. Additionally or alternatively, in some implementations, the mask type for the user interface includes a mask size. In some such implementations, the mask size includes extra-small, small, medium, large, extra-large or any reasonable intermediary size such as small/medium, etc. Additionally, or alternatively, in some implementations, the mask type for the user interface includes a mask model of the user interface. Additionally, or alternatively, in some implementations, the mask type for the user interface includes a mask manufacturer of the user interface.

Additionally, or alternatively, in some implementations, the mask type for the user interface includes a mask style. For example, the mask style can include face-mounted style, conduit style, or both. A face-mounted style mask generally refers to a mask that is generally positioned on the front of the user's face, with the conduit attached to the front of the mask at the front of the user's face. The face-mounted style mask may include one or more straps that extend around the user's head to secure the mask to the user's head. A face-mounted style mask is generally illustrated in FIG. 2. A conduit style mask, also referred to as a headgear mask or a headgear user interface, is a mask that includes its own conduit that extends around the user's head. The conduit from the respiratory therapy device is coupled to the conduit of the conduit style mask at the top of the user's head. The conduit of the conduit style mask then extends to the front of the user's face and are positioned in front of the user's mouth and/or nose, to provide air to the user's airway. In some implementations, the conduit style mask has a single conduit that extends on one side of the user's face. In other implementations, the conduit style mask has two conduits that extend on either side of the user's face.

In some implementations, the method 700 further includes step 740, where a flow-based mask type of the user interface is determined based at least in part on the analyzed flow data. In some such implementations, a corresponding likelihood (e.g., in the forms of a confidence interval, a probability, a score, a percentage, a ranking, Yes/No, descriptive words, etc.) for each of a plurality of mask types is determined for the flow-based mask type.

In some implementations, analyzing the received flow data (at step 730) and determining the flow-based mask type of the user interface (at step 740) can include determining a pressure versus flow rate curve for the user interface. Method 700 can include receiving pressure data associated with the respiratory therapy system, which may be received with the flow rate data (or in some implementations as an alternative to the flow rate data). The pressure versus flow rate curve can be used to determine the ratio of the pressure to the flow rate for various different pressures and flow rates. The ratio between pressure and flow rate can then be mapped to known ratios of pressure and flow rates for a plurality of different mask types. This mapping can be part of step 740, step 760, or a stand-alone step.

As discussed herein, in some implementations, a pathway is formed by a respiratory therapy device (e.g., the respiratory therapy device 122), a mask (e.g., the user interface 124), and a conduit (e.g., the conduit 126). The conduit creates a first impedance Z1 (humidifier tub, tube, and mask impedance), which in turn causes a pressure drop ΔP that is a function of the total flow rate Qt. The user interface (e.g., mask) pressure Pm is the device pressure Pd less the pressure drop ΔP through the conduit.

$$Pm=Pd-\Delta P \quad \text{Eq. 7}$$

where ΔP is the pressure drop, characteristic of the conduit. The pressure drop ΔP is a function of the total flow rate Qt:

$$\Delta P=Z1\cdot Qt \quad \text{Eq. 8}$$

In some implementations, the vent of the mask creates a second impedance Z2 (vent impedance). The mask interface pressure Pm is directly related to the vent flow rate Qv via the vent impedance characteristic Z2:

$$Pm=Z2\cdot Qv \quad \text{Eq. 9}$$

Similarly, the vent flow rate Qv is directly related to the mask interface pressure Pm via the vent admittance characteristic Y2:

$$Y2=\frac{1}{Z2} \quad \text{Eq. 10}$$

$$Qv=Y2\cdot Pm \quad \text{Eq. 11}$$

Combining equation (7) with equation (11), the vent flow rate Qv may be determined as:

$$Qv=Y2\cdot(Pd-\Delta P) \quad \text{Eq. 12}$$

An unintentional leak, which is unknown and unpredictably variable, creates a third impedance Z3 (leak impedance). Additionally, in some implementations, the fourth impedance (airway resistance and lung compliance) includes (i) the patient airway resistance Z4, (ii) the patient lung compliance Clung, and/or (iii) the variable pressure source Plung, each of which represents characteristics of the user's respiratory circuit. Thus, the total flow rate Qt is equal to the sum of the vent flow rate Qv, the leak flow rate Qleak, and the respiratory flow rate Qr:

$$Qt=Qv+Q\text{leak}+Qr \quad \text{Eq. 13}$$

In some implementations, the respiratory flow rate Qr averages to zero over a plurality of respiratory cycles (e.g., breathing cycles), because the average respiratory flow rate into or out of the lungs must be zero. Taking tilde (~) to indicate the average value over the plurality of respiratory cycles:

$$\tilde{Q}r=0 \quad \text{Eq. 14}$$

As such, taking an average of each flow rate over the plurality of respiratory cycles (e.g., breaths), the average leak flow rate may be approximated as:

$$\tilde{Q}\text{leak}=\tilde{Q}t-\tilde{Q}v \quad \text{Eq. 15}$$

The process of averaging may be implemented by low-pass filtering with a time constant long enough to contain the plurality of respiratory cycles. The time constant can be of any suitable duration, such as five seconds, ten seconds, thirty seconds, one minute, etc. However, other time intervals are also contemplated.

Combining equations (7), (8), and (9), the average device pressure P̃d may be written as:

$$\tilde{P}d=Z1\cdot\tilde{Q}t+Z2\cdot\tilde{Q}v \quad \text{Eq. 16}$$

In the absence of any leak flow (e.g., Q̃leak=0), the average total flow rate Q̃t is equal to the average vent flow rate Q̃v. Equation (16) can then be written to reflect the relationship between the average total flow rate Q̃t and the average device pressure P̃d that characterizes the respiratory therapy air circuit:

$$\tilde{P}d=Z1\cdot\tilde{Q}t+Z2\cdot\tilde{Q}t \quad \text{Eq. 17}$$

$$\tilde{P}d=(Z1+Z2)\cdot\tilde{Q}t \quad \text{Eq. 18}$$

$$\tilde{P}d=(Z1+Z2)\cdot\tilde{Q}v \quad \text{Eq. 19}$$

The relationship, is determined by the vent impedance characteristic Z2 and the conduit pressure drop impedance characteristic Z1. In the presence of leak, Q̃t>Q̃v. In the absence of leak, Q̃t=Q̃v.

Figure 8B:
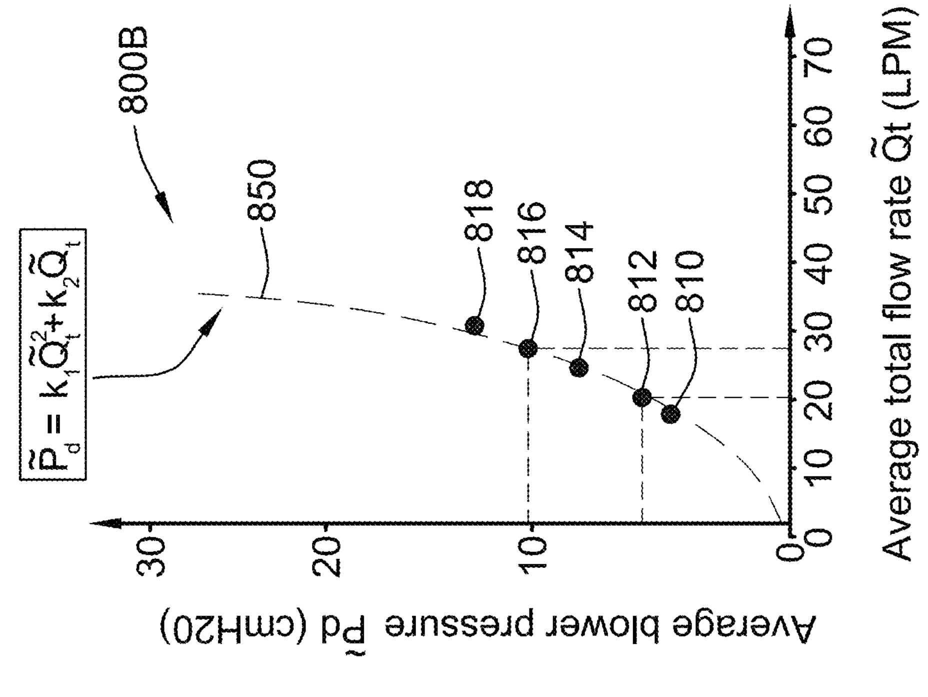
FIG. 8B illustrates a fitted characteristic curve over the plotted Cartesian coordinates of FIG. 5A, according to some implementations of the present disclosure.
Figure 8A:
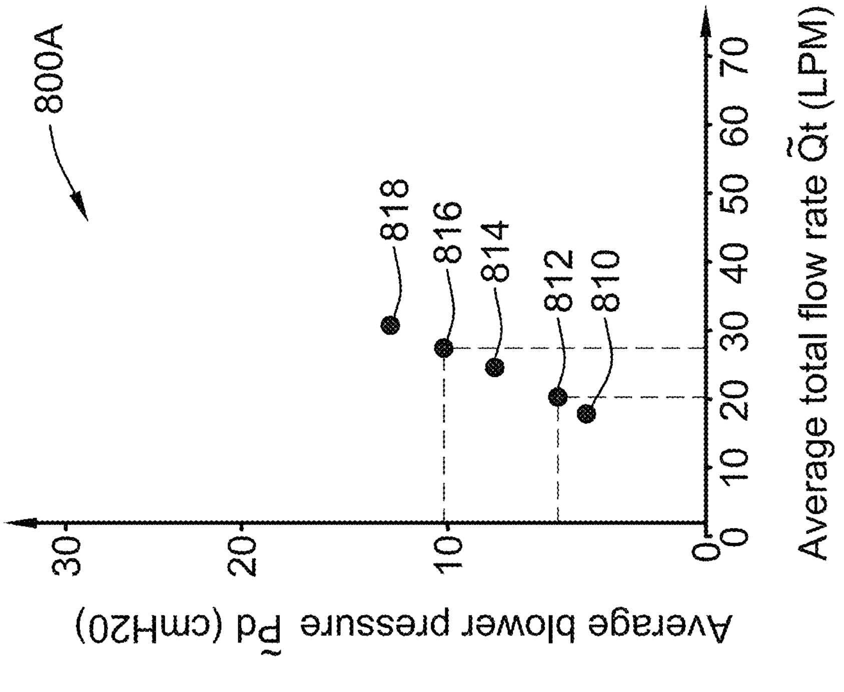
FIG. 8A illustrates plotted Cartesian coordinates representing average device pressure and average total flow rate expressed as liters per minute, according to some implementations of the present disclosure.

Referring now to FIG. 8A, a scatter plot 800A of average total flow rate Q̃t (in liters per minute) versus average device pressure P̃d (in $cmH_2O$) is depicted. FIG. 8A illustrates plotted Cartesian coordinates representing average device pressure and average total flow rate, expressed as liters per minute ("LPM," which is equivalent to 60 times L/s). Each Cartesian coordinate includes an X value and a Y value. As shown, five Cartesian coordinates 810, 812, 814, 816, and 818 are plotted in the scatter plot 800A over a period of therapy. Each Cartesian coordinate may also be expressed as (Q̃t, P̃d).

For example, a first Cartesian coordinate 812 has a first X value that is about 20 liters per minute, and a first Y value that is about 6 $cmH_2O$. As such, the first Cartesian coordinate 812 can be expressed as (20, 6). The first X value can be estimated and/or calculated based at least on a first plurality of flow rate values generated over a first time period. In some implementations, the first X value is an average flow rate value of the first plurality of flow rate values generated over the first time period.

In some implementations, the first time period is a predetermined time interval, such as five seconds, ten seconds, 30 seconds, one minute, two minutes etc. In some implementations, the first time period includes one or more full breathing cycles, such as one breathing cycle, two breathing cycles, five breathing cycles, ten breathing cycles, etc. Therefore, in some implementations, the first X value is the average flow rate value of the first plurality of flow rate values generated over one or more breathing cycles, such as seven breathing cycles (FIG. 6A).

Similarly, the first Y value can be estimated and/or calculated based at least on a first plurality of pressure values generated over the first time period. Each of the first plurality of pressure values corresponds with a respective one of the first plurality of flow rate values. For example, in some implementations, each of the first plurality of flow rate values has a corresponding time stamp (e.g., FIG. 6A). Using the corresponding time stamp, the respective one of the first plurality of pressure values can be identified (e.g., FIG. 6B or FIG. 6C). Therefore, in some implementations, the first Y value is the average pressure value of the first plurality of pressure values generated over one or more breathing cycles, such as seven breathing cycles (e.g., FIG. 6B or FIG. 6C).

A second Cartesian coordinate 816 has a second X value that is about 28 liters per minute, and a second Y value that is about 10 $cmH_2O$. As such, the second Cartesian coordinate 816 can be expressed as (28, 10). The second X value and the second Y value of the second Cartesian coordinate 816 can be estimated and/or calculated the same way as, or similar to, the first X value and the first Y value of first Cartesian coordinate 812.

Referring to FIG. 8B, based at least in part on the first Cartesian coordinate 812 and the second Cartesian coordinate 816, a pressure versus flow rate curve 850 can be fitted in the plot 800B. For example, in some implementations, the pressure versus flow rate curve 850 may be approximated using a polynomial equation, such as a quadratic equation:

$$\tilde{P}_d = k_1 \cdot \tilde{Q}_v^2 + k_2 \cdot \tilde{Q}_v \quad \text{Eq. 20}$$

The parameters of the pressure versus flow rate curve, in this quadratic equation, two non-zero constants (or coefficients), $k_1$ and $k_2$, characterize the series concatenation of the vent impedance characteristic Z1 and the air circuit pressure drop impedance characteristic Z2. In some implementations, the polynomial equation defines an intentional leak of the system (e.g., vent flow of the system) by providing a corresponding flow rate of intentional leak for a given pressure.

If at least two Cartesian coordinates are known, the non-zero constants $k_1$ and $k_2$ can be solved. For example, using the first Cartesian coordinate 812 (20, 6) and the second Cartesian coordinate 816 (28, 10), equation (20) can be solved and re-written as approximately:

$$\tilde{P}_d = \frac{1}{140}\tilde{Q}_v^2 + \frac{11}{70}\tilde{Q}_v \quad \text{Eq. 21}$$

In other words, the non-zero constant $k_1$ is $$\frac{1}{140}$$

(about 0.00714), and the non-zero constant $k_2$ is $$\frac{11}{70}$$

(about 0.157) for the quadratic curve going through the first Cartesian coordinate 812 and the second Cartesian coordinate 816. Therefore, in some implementations, the pressure versus flow rate curve 850 can be estimated and/or defined as equation (21).

In some implementations, the non-zero constants depend on (i) the unit for the pressure values, (ii) the unit for the flow rate values, (iii) the vent for the respiratory therapy system, (iv) the mask for the respiratory therapy system, (v) the humidifier tub for the respiratory therapy system, (vi) the conduit for the respiratory therapy system, (vii) computation scaling factors, or (viii) any combination thereof. The non-zero constants can also vary with different types of masks, different manufacturers of masks, and/or different batches of masks. For example, with the pressure values measured in $cmH_2O$ and the flow rate values measured in L/min, the non-zero constants $k_1$ and $k_2$ can be about $$\frac{1}{154}$$

and about $1/7$ respectively, for a particular vent of a respiratory therapy system.

In some implementations, the polynomial equation may have more than two non-zero constants, such as three non-zero constants, four non-zero constants, five non-zero constants, etc. For example, the polynomial equation may be expressed as:

$$\tilde{P}_d = k_1 \cdot \tilde{Q}_v^2 + k_2 \cdot \tilde{Q}_v + k_3 \quad \text{Eq. 22}$$

In some implementations, the polynomial equation may involve a power of three, four, five, etc. For example, the polynomial equation may be expressed as:

$$\tilde{P}_d = k_1 \cdot \tilde{Q}_v^3 + k_2 \cdot \tilde{Q}_v^2 + k_3 \cdot \tilde{Q}_v + k_4 \quad \text{Eq. 23}$$

In some implementations, unintentional leak is more likely to occur in a system where the pressure values are high. To get a better fitted intentional leak characteristic curve, only Cartesian coordinates with lower values are used to solve the polynomic equation. For example, in some implementations, the Cartesian coordinates where the Y values do not exceed a predetermined pressure threshold are used. The predetermined pressure threshold may be associated with a low likelihood of unintentional leak, such as less than about 10 $cmH_2O$, less than about 9 $cmH_2O$, less than about 8 $cmH_2O$, less than about 7 $cmH_2O$, less than about 6 $cmH_2O$, less than about 5 $cmH_2O$, less than about 4 $cmH_2O$, less than about 3 $cmH_2O$, or less than about 2 $cmH_2O$.

Figure 9:
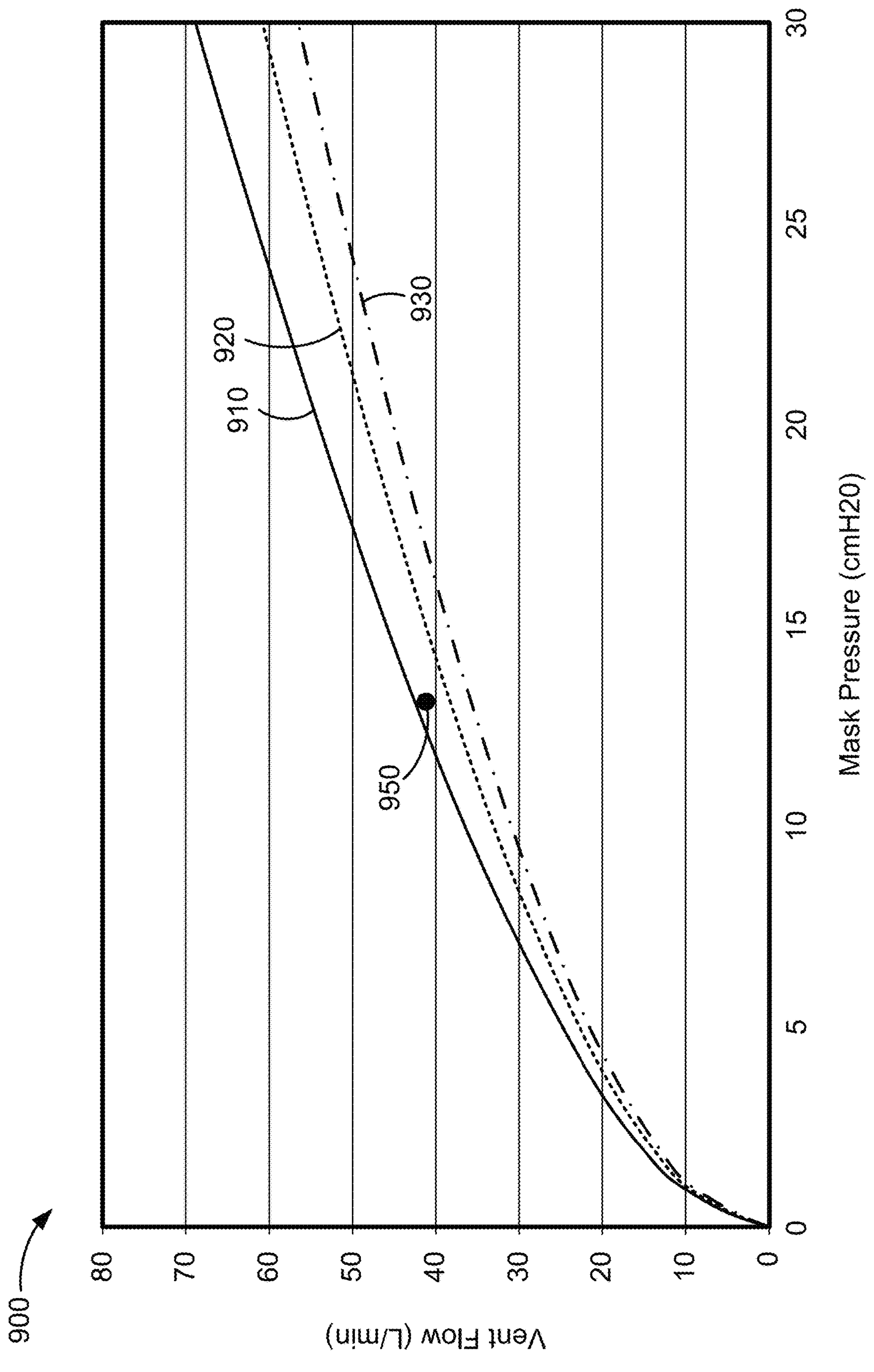
FIG. 9 illustrates mask identification curves of a user interface associated with a user, according to some implementations of the present disclosure.

FIG. 9 illustrates an X-Y plot 900 that can be used to determine the flow-based mask type of the user interface (e.g., to determine the type of user interface based on the flow rate data and/or the pressure data). The X-Y plot 900 illustrates three mask identification curves of a user interface associated with a user, according to some implementations of the present disclosure. In the illustrated example, the x-axis represents mask pressure, and the y-axis represents vent flow, but in other examples the x-axis may represent vent flow, and the y-axis may represent mask pressure. The three mask identification curves each represents a mask type. The mask identification curves can be predetermined standard curves and/or learned over time based on collected data by the respiratory therapy system.

Different masks can have different mask identification curves. As an example, a full face mask, a partial face mask, a nasal mask, and nasal pillows can all have different mask identification curves. As another example, different mask sizes (e.g., small, medium, large) can have different mask identification curves. As a further example, different mask styles (conduit style, face mounted style) can have different mask identification curves. As yet another example, masks made from different manufacturers can have different mask identification curves. As yet a further example, different mask models can have different mask identification curves.

In this example in FIG. 9, the first curve 910 is associated with a first mask; the second curve 920 is associated with a second mask; and the third curve 930 is associated with a third mask. As discussed herein, a ratio between a pressure value and a flow rate value can be mapped to standard characteristic curves. As shown, a point 950 representative of the ratio is mapped to the X-Y plot 900, and fits closest to the first curve 910. Thus, it is likely that the mask type is the first mask. In some implementations, the system 100 and/or the method 700 assigns the likelihood for each mask type. In this example, the first mask is the most likely, and the third mask is the least likely. Thus, in some implementations, flow data and/or pressure data can be used to generate a pressure versus flow curve for the user interface that the user is using. This pressure versus flow curve can then be compared to pre-existing pressure versus flow rate curves that are known to be associated with various types of user interfaces.

Figure 10B:
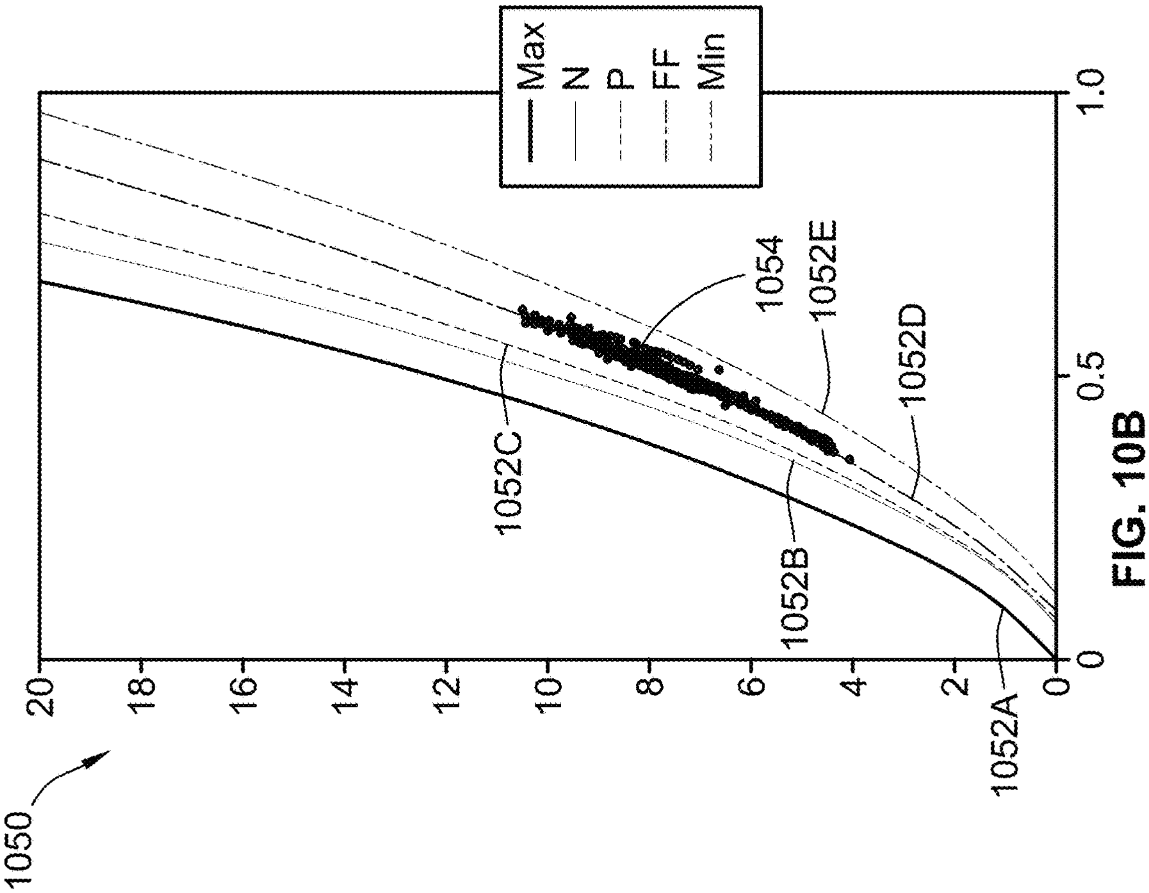
FIG. 10B illustrates a comparison between pressure versus flow rate data points, and known pressure versus flow rate curves for a plurality of mask types, according to some implementations of the pressure disclosure.
Figure 10A:
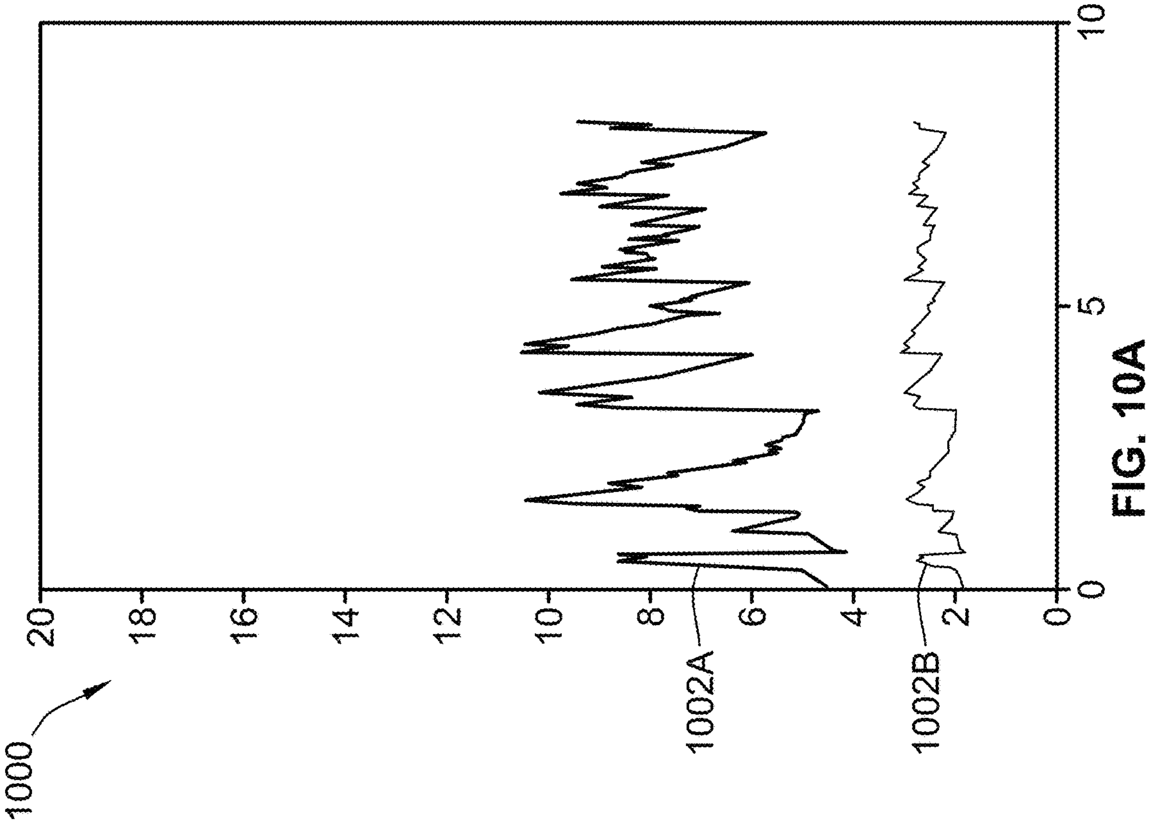
FIG. 10A illustrates a pressure signal and a flow rate signal, according to some implementations of the present disclosure.

FIGS. 10A and 10B illustrate further details regarding the identification of mask type using flow rate data and/or pressure data. FIG. 10A includes a plot 1000 that shows a pressure signal 1002A and a flow rate signal 1002B versus time. The pressure signal 1002A is plotted as $cmH_2O$, the flow signal is plotted as Liters per second, and the time is plotted as hours. Pressure signal 1002A and flow rate signal 1002B illustrate typical signals that can be obtained from analyzing the flow rate data.

FIG. 10B illustrates a plot 1050 with a series of known pressure versus flow rate curves 1052A-1052E, and a series of pressure versus flow rate data points 1054. The pressure versus flow rate data points 1054 are obtained from the pressure signal 1002A and the flow rate signal 1002B in FIG. 10B. In some implementations, each individual data point 1054 corresponds to the average pressure over a minute versus the average flow rate for that same minute. Each pressure versus flow rate curve 1052A-1052E corresponds to the pressure versus flow rate of a known type of mask. In the illustrated implementation, curve 1052A is a maximum pressure versus flow rate curve for a typical mask that may be used by the user. Curve 1052B is the pressure versus flow rate curve for a nasal mask. Curve 1052C is the pressure versus flow rate curve for a nasal pillow mask. Curve 1052D is the pressure versus flow rate curve for a full-face mask. Curve 1052E is a minimum pressure versus flow rate curve for a typical mask that may be used by the user. The maximum curve 1052A and the minimum curve 1052E can establish outer bounds for the pressure versus flow rate curves. If the data points 1054 fall outside of these outer bounds, that may indicate that the analysis of the flow rate data and the pressure data was faulty. It may also indicate that the user is using an unknown type of mask, or a mask from an unknown source. In one example, curves 1052A and 1052E can serve to establish the outer bounds for masks made by a specific manufacturer. If the data points 1054 fall outside of these outer bounds, it can be determined that the user is wearing a mask from a different manufacturer. As shown in FIG. 10B, a majority of the data points 1054 fall along curve 1052D, which is the pressure versus flow rate curve for a full-face mask. Thus, by analyzing the flow rate data and the pressure data to generate the data points 1054, it can be determined that there is a high likelihood that the user's current mask is a full-face mask.

While FIG. 10B shows three pressure versus flow rate curves corresponding to known masks, and also maximum and minimum pressure versus flow rate curves to establish outer bounds, any number of known pressure versus flow rate curves can be used. For example, in some implementations, method 700 may not include comparing the data points 1054 to the outer bounds established by curves 1052A and 1052E. In other implementations, method 700 may use curves that correspond to additional mask types, such as partial-face masks.

In some implementations, a single type of user interface is selected based on the analyzed flow rate data. In other implementations, the likelihood that the user interface corresponds to each type of known user interface is determined. In some implementations, the likelihood is expressed as a percentage, for example as a whole number between 1 and 100 or as a decimal number between 0 and 1. In other implementations, each type of know user interface can be assigned a likelihood score between 0 and 10. Additional details related to analyzing flow rate data to aid in identifying the mask can be found in International Application No. PCT/IB2021/051884 filed on May 3, 2021, which is hereby incorporated by reference herein in its entirety.

Referring back to FIG. 7, in some implementations, the method 700 further includes step 750, where an acoustic-based mask type of the user interface is determined based at least in part on the analyzed acoustic data. In some such implementations, a corresponding likelihood (e.g., in the forms of a confidence interval, a probability, a score, a percentage, a ranking, Yes/No, descriptive words, etc.) for each of a plurality of mask types is determined for the acoustic-based mask type.

In some implementations, analyzing the received acoustic data (at step 730) and determining the acoustic-based mask type of the user interface (at step 750) can include performing a variety of different analyses of the acoustic data to determine features or characteristics representative of the mask type. The analysis can include windowing the generated acoustic data based, at least in part, on at least one feature of the respiratory therapy system, such as at least one feature of the user interface, at least one feature of the conduit, etc. The at least one feature of the user interface can be, for example, the expansion from the connection of the conduit to the chamber formed by the cushion of a full face mask against a user's face. The at least one feature of the conduit can be, for example, the length of the conduit. More specifically, the length can be the distance from the acoustic sensor to where the conduit connects to the user interface. In one or more implementations, the windowing can be based, at least in part, on at least one feature of the one or more features of the user interface. The windowing is a selection of a portion of the generated acoustic data that is used for additional analysis and/or for characterizing the user interface, as discussed below. The windowing focuses in on the generated acoustic data that can differentiate and distinguish between the various user interfaces that exist for respiratory therapy systems. Accordingly, the windowing can focus in on the generated acoustic data that is indicative of the user interface. The windowing can beneficially allow regions of the signal that may otherwise confound the estimation of the user interface, such as varying conduit lengths, differences in respiratory therapy systems, such as different respiratory therapy devices, etc. to be ignored. Thus, windowing the generated acoustic data selects only the region of the acoustic signal, and the corresponding data, that is associated with the user interface. As a result, the windowing allows for ignoring regions of the acoustic signal, and the corresponding data, that may otherwise confound the estimation of the user interface, such as the factors discussed above.

The at least one feature has a corresponding point in the generated acoustic data that acts as fiducial point. The fiducial point provides a basis for analyzing the generated acoustic data for different types of user interfaces, conduits, respiratory therapy devices, etc. Thus, the fiducial point acts as a reference for further analysis of the generated acoustic data, and provides for consistency between different acoustic data generated under different circumstances.

In one or more implementations, the fiducial point can correspond to a location of the one or more features along a pathway formed, at least in part, by the conduit and the user interface. For example, the fiducial point can correspond to a feature of the conduit or a feature of the connection between the conduit and the user interface. In one or more implementations, the fiducial point can correspond to a feature of the user interface itself. In one or more implementations, the fiducial point is the same for a given user interface. In one or more implementations, the fiducial point is the same for all of the different possible user interfaces. The feature can be generic to different types of user interfaces so that the feature, or at least a variation of the feature, is present in all respiratory therapy systems that include a user interface connected to a conduit. For example, the feature can be the expansion of the acoustic pathway that occurs at the connection between a conduit and a user interface. Although such an expansion may not be identical for every combination of the conduit and different user interface, every combination of the conduit with a user interface can include such an expansion. Accordingly, the expansion at the connection between the conduit and the user interface can be the feature that corresponds to the fiducial point user in widowing of the generated acoustic data.

Broadly, the fiducial point can be any feature that causes a change in acoustic impedance and, therefore, is present in the generated acoustic data from the acoustic reflection. In one or more implementations, the change in the acoustic impedance can be based, at least in part, on a narrowing of the pathway formed by the conduit and the user interface and at (i) the user interface, (ii) a connection of the conduit and the user interface, or (iii) a combination thereof. Alternatively, the change in the acoustic impedance can be based, at least in part, on a widening of the pathway at (i) the user interface, (ii) a connection of the conduit and the user interface, or (iii) a combination thereof.

In one or more implementations further discussed below, the analysis of the generated acoustic data can include performing a deconvolution on the generated acoustic data, such as calculating the cepstrum of the generated acoustic data. In which case, the fiducial point can be a minimum point within a predetermined section of the deconvolution of the generated acoustic data. Alternatively, the fiducial point can be a maximum point within a predetermined section of the deconvolution of the generated acoustic data. As discussed above, the fiducial point can be based on the connection between the user interface and the conduit, and the predetermined section can be based on the length of the conduit. More specifically, the predetermined section can be based on the distance between the acoustic sensor and the connection between the conduit and the user interface.

Figure 11:
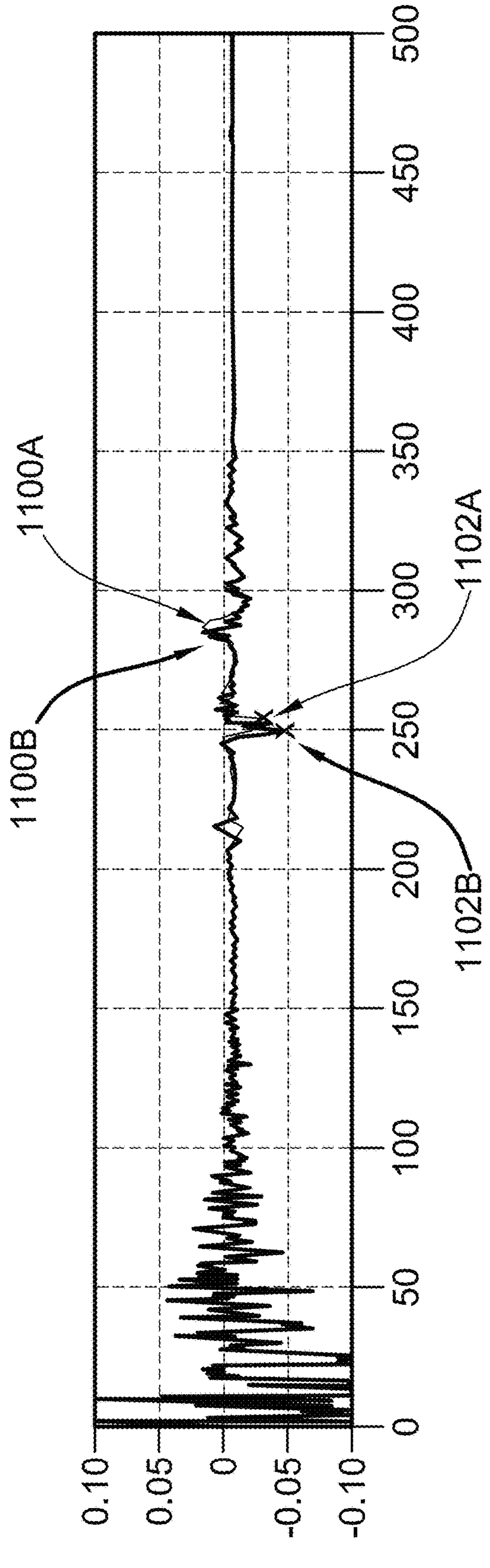
FIG. 11 is a plot of calculated cepstrums of generated acoustic data, according to some implementations of the present disclosure.

Referring to FIG. 11, illustrated are the calculated cepstrums 1100A and 1100B resulting from generated acoustic data for two different acoustic reflections. The two cepstrums 1100A and 1100B are shown merely for descriptive convenience and are not meant to be limiting. For example, a single cepstrum can be calculated for generated acoustic data for characterizing a user interface. The two cepstrums 1100A and 1100B are two cepstrums calculated from different generated acoustic data for the same user interface.

The plots are shown with quefrency in the X-axis and amplitude in the Y-axis. The quefrency is similar to time or distance, but the units of the X-axis are simply samples or sample numbers of the acoustic reflection. The units of the Y-axis can be any unit that measures the amplitude. Around the 250 value in the X-axis are large minima 1102A and 1102B, which can be used as fiducial points for analyzing the generated acoustic data. These correspond to a widening of the pathway in the conduit, such as the connection point between the conduit and the user interface.

In one or more implementations, the windowing can include a first windowing of the generated acoustic data and a second windowing of the generated acoustic data. In one or more implementations, the first windowing can identify or locate a feature of the user interface corresponding to the fiducial point. Subsequently, the second windowing can identify or locate further features of the user interface. The first windowing of the generated acoustic data can vary from the second windowing of the generated acoustic data by an amount of the generated acoustic data that is selected before the fiducial point in the generated acoustic data, after the fiducial point in the generated acoustic data, or a combination thereof. In relation to a length of the pathway resulting from the conduit and the user interface, the first windowing can capture only about 10 cm before and after the fiducial point, e.g., about 10 cm before and after connection point between the conduit and the user interface. In contrast, the second windowing can capture about 35 cm before the fiducial point and about 50 cm after the fiducial point.

The amount of data captured by the windowing can vary based on the amount of the generated acoustic data that is required for a specific analysis related to the windowing. For example, the first windowing may be merely to identify the fiducial point. As a result, the size of the resulting window of the windowing can be smaller because it is focused purely on determining the fiducial point. Once the fiducial point is determined, the second windowing can occur, which can result in a larger second window. The larger second window can capture the generated acoustic data that is sent to the characterizing step discussed below. The characterizing step may benefit from additional data, which is why the second window generated from the second windowing can be larger than the first window generated from the first windowing, with the larger window capturing more features for characterizing the user interface compared to the first window. Alternatively, the size of the windows generated during the first and second windowing can be reversed, with the first window being large than the second window. The first window being large may assist in determining the correct fiducial point for the analysis.

Figure 12:
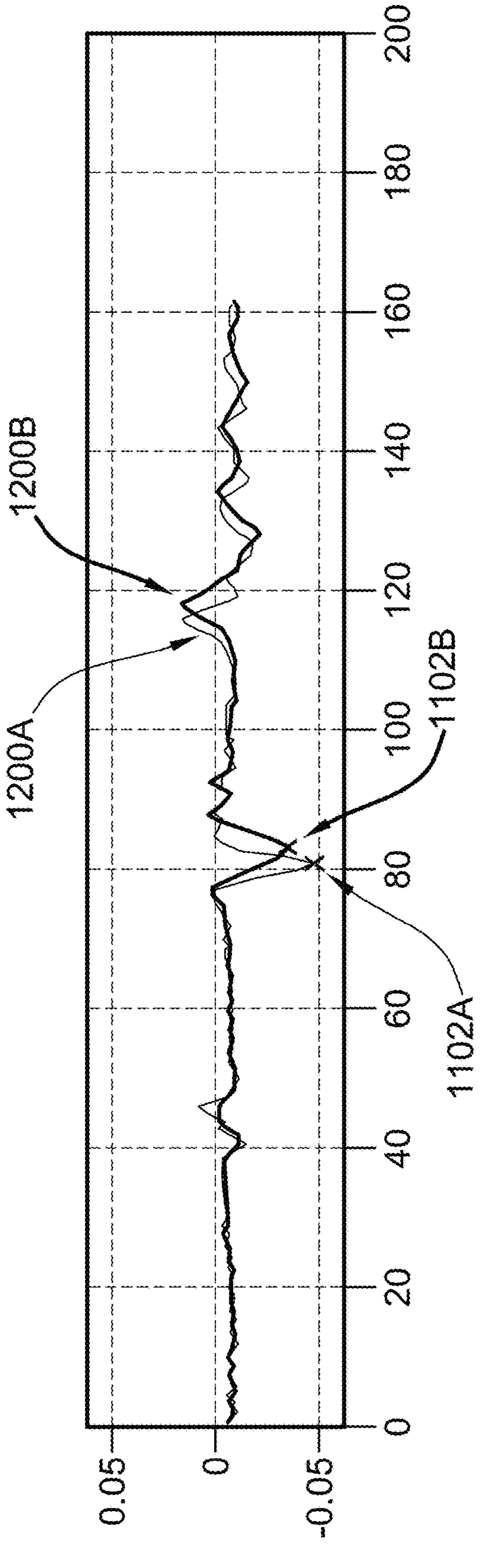
FIG. 12 is a plot of windowed cepstrums of generated acoustic data, according to some implementations of the present disclosure.

Referring to FIG. 12, the windowed cepstrums 1200A and 1200B, corresponding to cepstrums 1100A and 1100B, respectively, are shown after the windowing is performed as described above. The windowing removed the generated acoustic data after about the 350 value in the X-axis in FIG. 11, and removed the generated acoustic data before about the 200 value in the X-axis in FIG. 11. The windowing is performed to eliminate the generated acoustic data that is not used for characterizing the user interface, and that could potentially disrupt the additional analysis and characterization of the acoustic data for determining the user interface. The generated acoustic data that remains is about 80 on either side of the fiducial points 1102A and 1102B.

Figure 13:
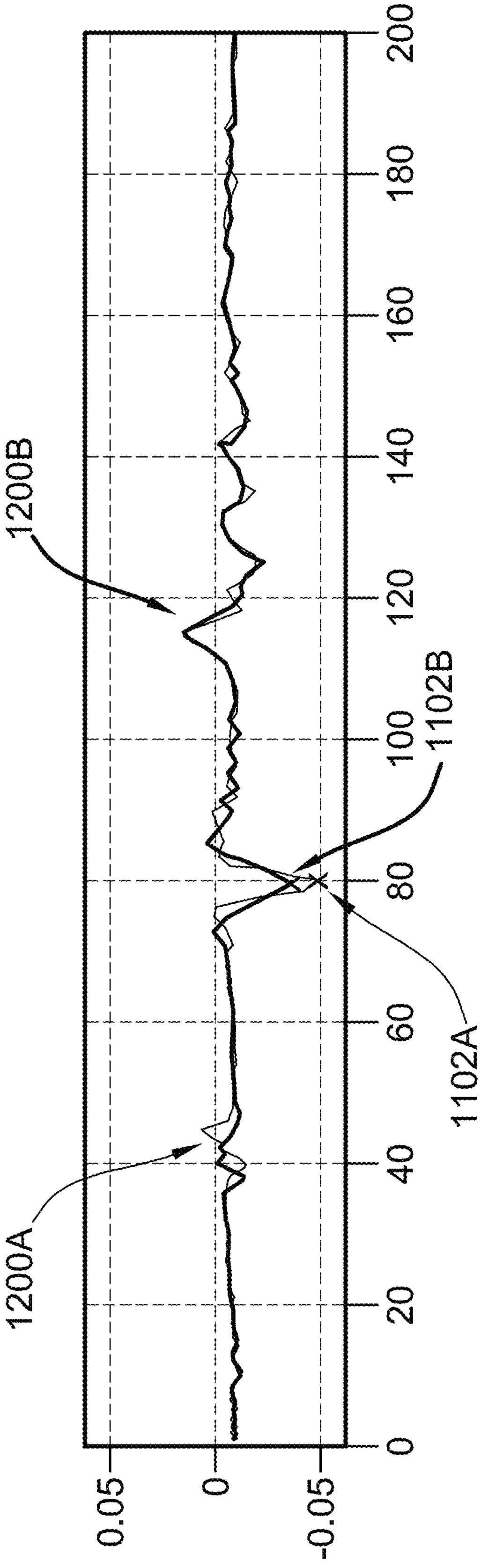
FIG. 13 is a plot of aligned windowed cepstrums of generated acoustic data, according to some implementations of the present disclosure.

Referring to FIG. 13, a further result of the windowing, as shown by the windowed cepstrum 1200A relative to the windowed cepstrum 1200B, is an alignment based on the fiducial points 1102A and 1102B. The alignment allows for further consistency in the additional analysis of the generated acoustic data and the characterizing of the analyzed acoustic data, as described below.

As discussed above, in one or more representations, the respiratory therapy system 120 analyzing the generated acoustic data can include a deconvolution of the generated acoustic data prior to the windowing of the generated acoustic data. In one or more implementations, the deconvolution of the generated acoustic data can include calculating a cepstrum of the generated acoustic data. The cepstrum identifies a distance associated with the acoustic reflection, and the distance indicates a location of the one or more features of the user interface. Calculating the cepstrum can be achieved by processing the acoustic reflection in a series of stages: calculate the frequency spectrum of the acoustic reflection via a fast Fourier transform; take the natural logarithm of the absolute magnitude of this frequency spectrum; and perform the inverse Fourier transform and calculate the real part of the signal to produce a cepstrum. This process may be repeated over multiple time intervals and an average cepstrum may be estimated. The resulting cepstrum signal transforms the acoustic reflection into the quefrency domain which is analogous to separating reflections in time and/or distance. In one or more implementations, the cepstrum can be calculated using a fast Fourier transform of 4096 samples of the acoustic reflection with, optionally, 50% overlap of the samples. These 4096 samples represent about 0.2 seconds of generated acoustic data.

In one or more implementations, the analyzing of the generated acoustic data can include calculating a derivative of the cepstrum to determine a rate of change of the cepstrum signal. The derivative of the cepstrum can provide additional information that is used to characterize the user interface. The derivative of the cepstrum also allows the network to find alternate features from the same input.

In one or more representations, the respiratory therapy system 120 analyzing the generated acoustic data can include normalizing the generated acoustic data. Normalizing the generated acoustic data can account for confounding conditions. The confounding conditions can be, for example, microphone gain, breathing amplitude, therapy pressure, varying conduit length, curled or stretched conduit, different therapy pressures, ambient temperature, or a combination thereof. In one or more implementations, the normalizing of the generated acoustic data can include subtracting a mean value from the generated acoustic data, dividing by a standard deviation of the generated acoustic data, or a combination thereof. The aim of the normalizing is to make all incoming of the cepstrums of the analyzed acoustic data of similar and magnitude and in a range that is natural for characterization, as further described below. In one or more implementations, the aim of the normalizing is to have the average of the cepstrum always be zero.

Figure 14:
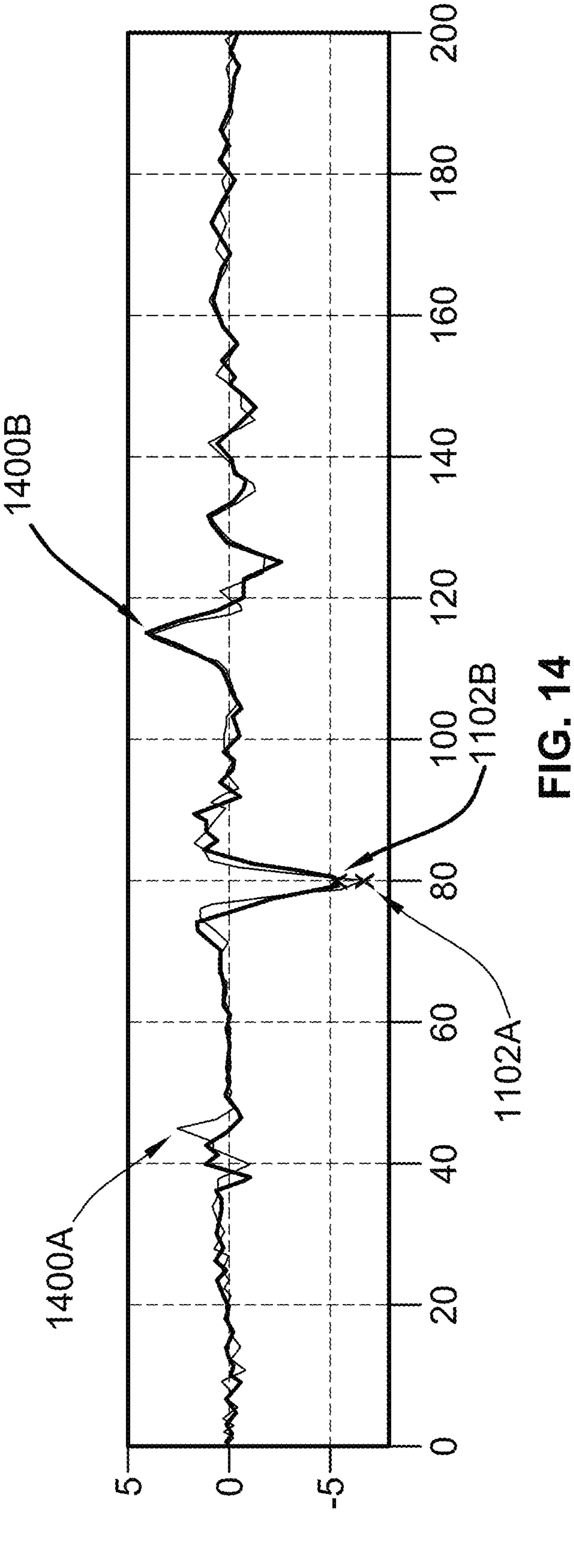
FIG. 14 is a plot of normalized windowed cepstrums of generated acoustic data, according to some implementations of the present disclosure.

Referring to FIG. 14, illustrated are the normalized cepstrums 1400A and 1400B, corresponding to cepstrums 1100A and 1100B, respectively. As shown by the values of the Y-axis in FIG. 14 relative to FIG. 13, the amplitudes have been adjusted so that the cepstrums are of similar magnitude and in a range that is natural characterization, as described below.

Referring back to FIG. 7, step 750 can include determining the mask type of the user interface based, at least in part, on the analyzed acoustic data. The determination can include inputting the analyzed acoustic data into a supervised machine learning model (e.g. a (deep) neural network such as a convolutional neural network) to determine the user interface. In one or more implementations, determining the user interface includes determining a form factor or type of the user interface (e.g. full face, nasal, pillow, etc.), a model of the user interface (e.g. AirFit™ F20 mask manufactured by ResMed), a size of one or more elements of the user interface, or a combination thereof.

In one or more implementations, the convolutional neural network (CNN) can include one or more convolutional and max pooling layers. In one or more implementations, the CNN can include one or more convolutional layers. In one or more implementations, the CNN can include N features. Each of the N features can be L samples in width. The CNN can further allow for a max pooling of M samples. Each feature of the N features is a unique plot or wave within the analyzed acoustic data, such as within the cepstrum. In one or more implementations, N can equal 64, such that the CNN can account for 64 unique plots or features within the analyzed acoustic data. Each sample of the L samples in width represents a data point generated based on the acoustic reflection. Thus, L samples represents L data points generated in response to the acoustic reflection. The L samples is matched roughly to the expected size of the features within the acoustic reflection. In one or more implementations, the L samples can be roughly correspond to about 25 cm in length. The M samples can be, for example, 20 samples, which allows for some natural time-invariance in the model to account for shifts between the different mask reflections. In one or more implementations, the ratio of N to M can be 1:1 to 4:1. In one or more implementations, the outputs of the convolutional layers can be fed into one or more fully-connected dense layers before a classification is made.

In one or more implementations, the CNN can be trained based on augment training set by adding random circular shift 20 samples to the features that are used to train the CNN. Specifically, a transformation can be applied to the features within the data set that is used to train the CNN, which makes for a more robust to time parts of the acoustic signal shifting, shifting the acoustic data in the windows, adding noise, and other types of shift for a more robust system.

In some implementations, the analyzed acoustic data can be used to identify the conduit based on the same methods disclosed for identifying the user interface. For example, different conduits (e.g., different diameters, lengths, materials, etc.) can be used within the respiratory therapy system. The systems and methods can be used to determine the different conduits.

In one or more implementations, the conduit can be identified instead of the user interface. In one or more implementations, the conduit can be identified along with identifying the user interface. Where both are identified, the order of identification and include both being identified at the same time, or one being identified first (e.g., the conduit or the user interface) followed by the other.

In one or more implementations, identifying the conduit interface can narrow down the possible choices from which to identify the user interface. For example, a specific conduit may be compatible with only a subset of all user interfaces for respiratory therapy systems. Accordingly, identifying the conduit can limit the subsequent identification of the user interface from among only the user interfaces within the subset.

In some implementations, a single type of user interface is selected based on the analyzed acoustic data. In other implementations, the likelihood that the user interface corresponds to each type of known user interface is determined. In some implementations, the likelihood is expressed as a percentage, for example as a whole number between 1 and 100 or as a decimal number between 0 and 1. In other implementations, each type of know user interface can be assigned a likelihood score between 0 and 10.

In additional or alternative implementations, analyzing the acoustic data can also include identifying one or more features to determine an acoustic signature of the mask. The analysis of the acoustic data can include generated a spectrum, generating a cepstrum, generating various different transforms or other operations of the spectrum and/or cepstrum, and other techniques. One or more can form an acoustic signature of the mask that the user is currently using. This acoustic signature can then be compared to known acoustic signatures of a variety of different types of masks, to aid in identify the mask that the user is currently using.

Additional details related to analyzing acoustic data to aid in identifying the mask can be found in U.S. Provisional Patent Application No. 63/108,161 filed on Oct. 30, 2020, U.S. Provisional Patent Application No. 63/107,763 filed on Oct. 30, 2020, and U.S. Provisional Patent Application No. 63/036,303 filed on June 8, 2020, each of which is hereby incorporated by reference herein in its entirety.

Referring back to FIG. 7, determining the mask type for the user interface (step 760) can include determining the mask type based at least in part on the determined flow-based mask type (step 740) and the determined acoustic-based mask type (step 750). As noted herein, the analysis of flow rate data, pressure data, and/or acoustic data can be used to identify the type of vent of the mask that the user is currently using, and the identified vent can then be correlated with a type of mask having that type of vent. In some implementations, a weighted likelihood can be generated for each of a plurality of mask types, based at least in part on the determined flow-based mask type (step 740) and the determined acoustic-based mask type (step 750), which may be a part of step 760 or its standalone step. Then, one of the plurality of mask types with a highest weighted likelihood can be selected as the mask type for the user interface (step 760).

For example, the method 700 may assign the determined flow-based mask type (step 740) and the determined acoustic-based mask type (step 750) equal weight (e.g., 50/50). Then, the weight for each mask type can be modified based on other factors (e.g., the length of time during which data is collected, the strength and/or quality of the flow signal and/or the acoustic signal, historical data, user input data). Table 1 below provides an illustrative example of the determined flow-based mask types (step 740), the determined acoustic-based mask types (step 750), the modified likelihood for each of the mask types, and the weighted likelihood for each of the mask types. In this case, the flow determination is weighted at 40%, while the acoustic determination is weighted at 60%. Thus, the likelihood of the flow-based determinations of the mask type are multiplied by 0.4, and the likelihood of the acoustic-based determinations of the mask type are multiple by 0.6. Then, the modified likelihoods can be added together to obtain the weighted likelihood for each mask type. As shown in the last column of this example, Type BB has the highest weighted likelihood. Therefore, it can be determined that the mask type for the user interface is Type BB (step 760).

TABLE 1

| Likelihood by Mask Type (scored 1-10 with 10 being the highest likelihood) | | | | | |
|---|---|---|---|---|---|
| Mask Type | Likelihood (Flow) | Likelihood (Acoustic) | Modified Likelihood (Flow) | Modified Likelihood (Acoustic) | Weighted Likelihood |
| AA | 5 | 6 | 2 | 3.6 | 5.6 |
| BB | 8 | 7 | 3.2 | 4.2 | 7.4 |
| CC | 3 | 5 | 1.2 | 3 | 4.2 |
| DD | 3 | 3 | 1.2 | 1.8 | 3 |

In some implementations, the method 700 further includes determining and/or estimating, for the flow-based mask type, a flow signal quality associated with the received flow data. For example, the flow signal quality can be determined and/or estimated based at least in part on the received flow data (step 710) or the analyzed flow data (step 730). Additionally or alternatively, in some implementations, the method 700 further includes determining and/or estimating, for the acoustic-based mask type, an acoustic signal quality associated with the received acoustic data. For example, the acoustic signal quality can be determined and/or estimated based at least in part on the received acoustic data (step 720) or the analyzed acoustic data (step 730).

In some implementations, the flow data and the acoustic data can be generated and/or received for a plurality of periods and/or sections over a sleep session. As the flow data and the acoustic data build up, if the signal quality of either data in a period/section is poor, the data from that period/section can be ignored in the analysis step (530) or determination step (760). Causes for poor signal qualify include: a leak in the respiratory therapy system, a movement associated with the user and/or one or more components of the respiratory therapy system, sensor issues (such as one or more sensor faults), one or more blocked vents, one or more damaged vents, etc.

Moreover, the weighted confidence interval discussed herein may be determined and/or modified based at least in part the flow signal quality and/or the acoustic signal quality. Then, in some implementations, one of the plurality of mask types with a highest modified weighted likelihood can be selected as the mask type for the user interface (step 760).

In some implementations, the method 700 (FIG. 7) further includes estimating a suitability of the determined mask type for a particular user. For example, the mask types tried by a particular user can be ranked. In some implementations, the method 700 can observe data collected during the transitioning from a full face mask to a nasal mask (or the reverse), and/or from a fabric mask to a silicone mask, etc., and determine which one is more suitable, e.g., works best, for the particular user. In some implementations, the suitability for a specific mask (e.g., identified from other steps in the method 700) can be estimated, based at least in part on, for example, one or more measured sleep-related parameters as described herein, such as the measured AHI scores, measured leaks (e.g., unintentional leaks such as mask leaks or mouth leaks), or user comfort (based on, for example, subject feedback from the user for each mask type tested).

In an example, the suitability for a specific mask, identified from other steps in the method 700, can be estimated based on one or more sleep-related parameters (such as AHI score) measured in respect of a specific mask worn by the user. The suitability may be assessed in comparison to other mask type(s) worn by the user, such as during the same or different sleep sessions or a mask-fitting session, and the one or more sleep-related parameters measured in respect of those other mask type(s) wherein the more (or most) favorable the sleep-related parameters, the more suitable the mask. In the present example, wherein the one or more sleep-related parameters includes a AHI score, the mask type resulting in the lowest AHI score for a user may be deemed the most suitable mask type for the user. In other examples, the most suitable mask type may be based on the identified mask resulting in a lower (or lowest) unintentional leak, a lower (or lowest) mouth leak, a longer (or longest) usage of respiratory therapy during the night, a higher/more favorable (or highest/most favorable) sleep quality metric, or any combination thereof.

In some implementations, method 700 can be used to categorize the mask as a specific mask type, e.g., full-face, partial face, nasal, or nasal pillows. In some implementations, method 700 is used to further identify the mask, for example by identifying the specific type and model of the mask.

Generally, the method 700 can be implemented using a system having a control system with one or more processors, and a memory storing machine readable instructions. The controls system can be coupled to the memory, and the method 700 can be implemented when the machine readable instructions are executed by at least one of the processors of the control system. The method 700 can also be implemented using a computer program product (such as a non-transitory computer readable medium) comprising instructions that when executed by a computer, cause the computer to carry out the steps of the method 700.

While the system 100 and method 700 have been described herein with reference to a single user, more generally, the system 100 and the method 700 can be used with a plurality of users simultaneously (e.g., two users, five users, 10 users, 20 users, etc.). For example, the system 100 and method 700 can be used in a cloud monitoring setting.

One or more elements or aspects or steps, or any portion(s) thereof, from one or more of any of the claims-below can be combined with one or more elements or aspects or steps, or any portion(s) thereof, from one or more of any of the other claims below, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method for identifying a user interface, the method comprising:

receiving flow data associated with air flowing in a respiratory therapy system;

receiving acoustic data associated with the respiratory therapy system;

analyzing the received flow data and the received acoustic data;

determining, based at least in part on the analyzed flow data, a flow-based probability for the user interface;

determining, based at least in part on the analyzed acoustic data and the flow-based probability, a mask type for the user interface; and performing an action based at least in part on the determination of the mask type for the user interface.

2. The method of claim 1, wherein the action includes adjusting one or more settings of the respiratory therapy system.

3. The method of claim 1, wherein the action includes determining a suitability of the determined mask type for the user interface based at least in part on a value of at least one sleep-related parameter measured while a user of the respiratory therapy system is wearing the user interface.

4. The method of claim 3, wherein determining the suitability of the determined mask type for the user interface includes comparing the value of the at least one sleep-related parameter while the user is wearing the user interface having the determined mask type to the value of the at least one sleep-related parameter while the user is wearing one or more user interfaces each having a mask type other than the determined mask type.

5. The method of claim 3, wherein the at least one sleep-related parameter includes an apnea-hypopnea index (AHI) value, an amount of unintentional leak, or both, and wherein the suitability of the determined mask type for the user interface is based at least in part on the AHI value with the determined mask type, whether the unintentional leak is present with the determined mask type, or both.

6. The method of claim 1, wherein the determined mask type for the user interface is one of a plurality of potential mask types, and wherein determining the flow-based probability includes assigned a flow-based probability to each of the plurality of potential mask types for the user interface, such that determining the mask type for the user interface is based on the analyzed acoustic data and the flow-based probability of each of the plurality of potential mask types.

7. The method of claim 6, wherein the flow-based probability assigned to at least one of the plurality of potential mask types is 0.

8. The method of claim 7, wherein determining the mask type for the user interface includes:

determining an acoustic-based probability for each mask type of the plurality of potential mask types having a flow-based probability that is greater than 0; and selecting the one of the plurality of potential mask types having the flow-based probability greater than 0 that has a highest acoustic-based probability.

9. The method of claim 6, wherein the flow-based probability assigned to each of the plurality of potential mask types is greater than 0.

10. The method of claim 1, wherein the determined mask type for the user interface (a) is (i) full face, (ii) partial face, (iii) nasal, or (iv) nasal pillows, (b) includes a mask size, or (c) both (a) and (b).

11. The method of claim 1, wherein the determined mask type for the user interface includes a mask style, a mask model, a mask manufacturer, or any combination thereof.

12. The method of claim 1, wherein the acoustic data is received from a microphone of the respiratory therapy system, and wherein the microphone is:

coupled to a smart device, a smart phone, a smart speaker, or any combination thereof; or coupled to (i) a conduit of a respiratory therapy device of the respiratory therapy system, (ii) a circuit board of the respiratory therapy device of the respiratory therapy system, (iii) a connector of the respiratory therapy system, (iv) the user interface of the respiratory therapy system, or (v) any other component of the respiratory therapy system.

13. The method of claim 12, wherein the respiratory therapy device is configured to supply pressurized air, via the user interface, to an airway of the user during a sleep session, and wherein the respiratory therapy device is configured for attachment to the user interface via the conduit, and wherein the respiratory therapy device, the user interface, and the conduit form a pathway such that, when the user interface is coupled to a face of the user, the supplied pressurized air is directed to the airway of the user.

14. The method of claim 1, wherein the analyzing the acoustic data includes performing a Cepstrum analysis, an autocepstrum analysis, an auto-correlation analysis, a spectral analysis, or any combination thereof.

15. The method of claim 1, wherein analyzing the acoustic data includes processing the received flow data and the received acoustic data to identify a plurality of features that includes (i) a spectral signature, (ii) a frequency, (iii) an amplitude, (iv) a change in any of (i)-(iii) relative to a baseline value, or (v) a combination thereof.

16. The method of claim 1, wherein the flow data includes flow rate data associated with a flow rate of air flowing in the respiratory therapy system, and pressure data associated with a pressure of the air flowing in the respiratory therapy system.

17. The method of claim 16, wherein analyzing the flow data includes:

determining a ratio of at least one pressure value of the received pressure data to at least one flow rate value of the received flow rate data; and mapping the ratio to one or more predetermined ratios of pressure to flow rate, each of the one or more predetermined ratios corresponding to one of a plurality of potential mask types for the user interface.

18. The method of claim 17, wherein determining the flow-based probability for the user interface is based at least in part on the mapping of the ratio of the at least one pressure value of the received pressure data to the at least one flow rate value of the received flow rate data.

19. A system for identifying a user interface, the system comprising:

a control system including one or more processors; and a memory having stored thereon machine-readable instructions;

wherein the control system is coupled to the memory, and at least one of the one or more processors of the control system is configured to execute the machine-readable instructions to:

receiving flow data associated with air flowing in a respiratory therapy system;

receiving acoustic data associated with the respiratory therapy system;

analyzing the received flow data and the received acoustic data;

determining, based at least in part on the analyzed flow data, a flow-based probability for the user interface;

determining, based at least in part on the analyzed acoustic data and the flow-based probability, a mask type for the user interface; and performing an action based at least in part on the determined mask type for the user interface.

20. The system of claim 19, further comprising the respiratory therapy system.

* * * * *